United States Patent
Morris

(10) Patent No.: US 9,687,016 B2
(45) Date of Patent: Jun. 27, 2017

(54) FATTY ACID FORMULATIONS AND METHODS OF USE THEREOF

(75) Inventor: Claudia R. Morris, Oakland, CA (US)

(73) Assignee: CHILDREN'S HOSPITAL & RESEARCH CENTER OAKLAND, Oakland, CA (US)

( * ) Notice: Subject to any disclaimer, the term of this patent is extended or adjusted under 35 U.S.C. 154(b) by 973 days.

(21) Appl. No.: 13/439,192

(22) Filed: Apr. 4, 2012

(65) Prior Publication Data

US 2012/0190737 A1 Jul. 26, 2012

Related U.S. Application Data

(62) Division of application No. 12/033,431, filed on Feb. 19, 2008.

(60) Provisional application No. 60/981,262, filed on Oct. 19, 2007, provisional application No. 60/891,097, filed on Feb. 22, 2007.

(51) Int. Cl.
*A23L 33/15* (2016.01)
*A23L 33/12* (2016.01)

(52) U.S. Cl.
CPC ............... *A23L 33/15* (2016.08); *A23L 33/12* (2016.08); *A23V 2002/00* (2013.01)

(58) Field of Classification Search
CPC ...... A23L 33/15; A23L 33/12; A23V 2002/00
USPC ........................................................ 514/739
See application file for complete search history.

(56) References Cited

U.S. PATENT DOCUMENTS

| | | | |
|---|---|---|---|
| 5,776,978 A | 7/1998 | Bruzzese | |
| 6,184,251 B1 | 2/2001 | Stordy et al. | |
| 6,426,362 B1* | 7/2002 | Miller et al. | 514/458 |
| 6,914,073 B2 | 7/2005 | Boulos et al. | |
| 7,169,385 B2 | 1/2007 | Fantuzzi et al. | |
| 7,534,450 B2 | 5/2009 | Walsh et al. | |
| 2003/0144219 A1 | 7/2003 | Phinney et al. | |
| 2004/0048919 A1 | 3/2004 | Dreon et al. | |
| 2004/0234587 A1 | 11/2004 | Sampalis | |
| 2005/0008690 A1 | 1/2005 | Miller | |
| 2005/0070498 A1 | 3/2005 | Ernest | |
| 2005/0249823 A1* | 11/2005 | Murphy et al. | 424/692 |
| 2005/0260181 A1 | 11/2005 | Girsh | |
| 2006/0052446 A1 | 3/2006 | Chilton et al. | |
| 2006/0062859 A1 | 3/2006 | Blum et al. | |
| 2006/0088574 A1* | 4/2006 | Manning et al. | 424/439 |
| 2006/0280840 A1 | 12/2006 | Robertson | |
| 2007/0031538 A1 | 2/2007 | Konuklar et al. | |

FOREIGN PATENT DOCUMENTS

| | | |
|---|---|---|
| WO | WO-03-082339 | 10/2003 |
| WO | WO-2004-004638 | 1/2004 |
| WO | WO-2006-071342 | 7/2006 |

OTHER PUBLICATIONS

NorishLife, "SpeakTM—SpeechNutrients", accessed online at <http://www.speechnutrients.com/products/speak> on Nov. 4, 2013, pp. 1-5.*
Amminger, et al. "Omega-3 fatty acids supplementation in children with autism: a double-blind randomized placebo-controlled pilot study", Biol. Psychiatry, vol. 61, 2007, pp. 551-553.
Buie, et al., "Recommendations for Evaluation and Treatment of Common Gastrointestinal Problems in Children with ADSs", Pediatrics, 2010, vol. 125, pp. S19-S29.
Morris, et al., "Syndrome of Allergy, Apraxia, and Malabsorption: Characterization of a Neurodevelopment Phenotype that Responds to Omega 3 and Vitamin E Supplementation", Alternative Therapies, 2009, vol. 15, No. 4, pp. 34-43.
Williams, et al., "Impaired Carbohydrate Digestion and Transport and Mucosal Dysbiosis in the Intestines of Children with Autism and Gastrointestinal Disturbances", PLoS One, 2011, vol. 6, Issue 9, pp. 1-21.

* cited by examiner

*Primary Examiner* — Sharmila G. Landau
*Assistant Examiner* — Sheridan Macauley
(74) *Attorney, Agent, or Firm* — Bozicevic Field & Francis, LLP; Paula A. Borden

(57) ABSTRACT

The present invention provides dietary formulations comprising polyunsaturated fatty acids and vitamin E. The present invention further provides methods of treating various conditions, generally involving administering to an individual in need thereof an effective amount of a subject dietary formulation.

11 Claims, No Drawings

FATTY ACID FORMULATIONS AND METHODS OF USE THEREOF

CROSS-REFERENCE

This application claims the benefit of U.S. Provisional Patent Application No. 60/891,097, filed Feb. 22, 2007, and of U.S. Provisional Patent Application No. 60/981,262, filed Oct. 19, 2007, which applications are incorporated herein by reference in their entirety.

BACKGROUND

Apraxia of speech is a neurologically based motor planning disorder of unknown etiology. Approximately half of children with autistic spectrum disorders have some degree of apraxia, although not all apraxic children are autistic. Children with apraxia find it very difficult to correctly pronounce sounds, syllables, and words. Some children remain speechless and require the use of augmentative communication devices or utilize a picture exchange communication system. Many children with apraxia present with homogeneous symptoms of neurological dysfunction that affect coordination, muscle tone, and sensory issues in addition to speech production difficulties, suggesting a common underlying mechanism of disease in these children. Standard treatment generally involves speech therapy with a speech pathologist knowledgeable in apraxia.

There is a need in the art for alternative approaches to treatment of apraxia.

LITERATURE

U.S. Pat. Nos. 5,776,978; 6,914,073; 7,169,385; 6,184,251.

SUMMARY OF THE INVENTION

The present invention provides dietary formulations comprising polyunsaturated fatty acids and vitamin E. The present invention further provides methods of treating various conditions, generally involving administering to an individual in need thereof an effective amount of a subject dietary formulation.

DEFINITIONS

"Fatty acids" refer to a family of carboxylic acids having a hydrocarbon chain of from about 12 to about 24 carbons in length. Unsaturated fatty acids have at least one carbon-carbon double bond in the hydrocarbon chain. Unsaturated fatty acids include monounsaturated fatty acids and polyunsaturated fatty acids (PUFAs). Unsaturated fatty acids are designated by the position of the first double bond from the methyl end of the hydrocarbon chain. Omega-3 fatty acids have a first double bond at the third carbon from the methyl end of the chain; and include, e.g., α-linolenic acid (octadeca-9,12,15-trienoic acid), stearidonic acid (octadeca-6,9,12,15-tetraenoic acid), eicosapentaenoic acid (eicosa-5,8,11,14,17-pentaenoic acid; "EPA"), docosapentaenoic acid (docosa-7,10,13,16,19-pentaenoic acid), eicosatetraenoic acid (eicosa-8,11,14,17-tetraenoic acid), and docosahexaenoic acid (docosa-4,7,10,13,16,19-hexaenoic acid; "DHA"). Omega-6 fatty acids have a first double bond at the sixth carbon from the methyl end of the chain; and include, e.g., linoleic acid (9,12-octadecadienoic acid), γ-linolenic acid (6,9,12-octadecatrienoic acid; GLA), eicosadienoic acid (11,14-eicosadienoic acid), dihomo-γ-linolenic acid (8,11,14-eicosatrienoic acid), arachidonic acid (5,8,11,14-eicosatetraenoic acid), docosadienoic acid (13,16-docosadienoic acid), adrenic acid (7,10,13,16-docosatetraenoic acid), docosapentaenoic acid (4,7,10,13,16-docosapentaenoic acid), and calendic acid (8E,10E,12Z-octadecatrienoic acid), and the like. Omega-9 fatty acids have a first double bond at the ninth carbon from the methyl end of the chain; and include, e.g., oleic acid (cis-9-octadecenoic acid); eicosenoic acid (cis-11-eicosenoic acid); mead acid (all-cis-5,8,11-eicosatrienoic acid); erucic acid (cis-13-docosenoic acid); and nervonic acid (cis-15-tetracosenoic acid).

As used herein, "vitamin E" refers to a family of eight molecules having a chromanol ring (chroman ring with an alcoholic hydroxyl group) and a 12-carbon aliphatic side chain containing two methyl groups in the middle and two more methyl groups at the end. The side chain of the tocopherols is saturated, while the side chain of the tocotrienols contain three double-bonds, all of which adjoin a methyl group. The tocopherols and the tocotrienols exist in four isoforms, referred to as alpha, beta, gamma and delta isoforms. The isoforms are named on the basis of the number and position of the methyl groups on the chromanol ring. The alpha form has three methyl groups, the beta and gamma forms have two methyl groups and the delta for has only one methyl group. As used herein, "vitamin E" refers to one or more of α-tocopherol, β-tocopherol, γ-tocopherol, α-tocotrienol, β-tocotrienol, and γ-tocotrienol. "Vitamin E" also includes esters of a vitamin E isoform. For example, "vitamin E" includes esters of a tocopherol, including acetates and succinates.

As used herein, the term "lipoic acid" refers to α-lipoic acid, which is a chiral molecule also known as thioctic acid; 1,2-diethylene-3 pentanoic acid; 1,2-diethylene-3 valeric acid; and 6,8-thioctic acid. Unless specified the term "lipoic acid" encompasses the racemic mixture as well as any other (non-50/50) mixture of the enantiomers including substantially pure forms of either the R-(+) or the S-(−) enantiomer. Further, unless specified otherwise the term covers pharmaceutically acceptable salts (e.g. Na and K salts) and amides, esters and metabolites of the acid. The molecule formula is $C_8H_{14}O_2S_2$ the molecular weight is 206.32 and it has a pKa of 4.7. In referring to pharmaceutically acceptable salts, the term is intended to encompass a conventional term of pharmaceutically acceptable acid addition salts which refer to salts which retain the biological effectiveness and properties of the free-base form of the acid and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malconic acid, succinic acid, maleic acid, fumaric, tartaric acid, citric acid, benzoic acid, cinnamic acid, mandelic acid, methanesulfonic acid, ethanesulfonic acid, p-toluenesulfonic acid, salicylic acid and the like. The same is true with respect to amides, esters and metabolites which can be formed and maintain biological effectiveness and not have significant undesirable biological properties.

"Carnitine" is also known as 3-carboxy-2-hydroxy-N,N,N-trimethyl-1-propanaminium hydroxide, inner salt; (3-carboxy-2-hydroxypropyl)trimethylammonium hydroxide, inner salt; gamma-amino-beta-hydroxybutyric acid trimethylbetaine; gamma-trimethyl-beta-hydroxybutyrobetaine; 3-hydroxy-4-(trimethyl-ammonio)butanoate. As used herein, the term "carnitine" includes carnitine and "carnitine analogs" and encompasses racemic or essentially pure L-carnitine (carnitine), or a corresponding alkanoyl-carnitine such as acetyl-carnitine or propionyl-carnitine, or a suitable salt of such compounds such as L-carnitine tartrate, L-carnitine fumarate, L-carnitine-magnesium-citrate, acetyl-L-carnitine tartrate, acetyl-L-carnitine-magnesium-citrate, or any mixture of the aforementioned compounds.

As used herein, "pharmaceutically acceptable carrier" includes any material which, when combined with an active ingredient of a composition, allows the ingredient to retain biological activity and without causing disruptive reactions with the subject's immune system. Examples include, but are not limited to, any of the standard pharmaceutical carriers such as a phosphate buffered saline solution, water, emulsions such as oil/water emulsion, and various types of wetting agents. Exemplary diluents for aerosol or parenteral administration are phosphate buffered saline or normal (0.9%) saline. Compositions comprising such carriers are formulated by well known conventional methods (see, for example, Remington's Pharmaceutical Sciences, Chapter 43, 14th Ed. or latest edition, Mack Publishing Co., Easton, Pa. 18042, USA; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) reducing the incidence and/or risk of relapse of the disease during a symptom-free period; (b) relieving or reducing a symptom of the disease; (c) preventing the disease from occurring in a subject which may be predisposed to the disease but has not yet been diagnosed as having it; (d) inhibiting the disease, i.e., arresting its development (e.g., reducing the rate of disease progression); (e) reducing the frequency of episodes of the disease; and (f) relieving the disease, i.e., causing regression of the disease.

The terms "individual," "host," "subject," and "patient," used interchangeably herein, refer to a mammal, e.g., a human. Where the host is a mammal, the subject will generally be a human, but may also be a domestic livestock (e.g., horse, cattle, pigs, goats, sheep, etc.), a mammalian laboratory subject (e.g., a rodent, a lagomorph, etc.), or mammalian pet animal.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an omega-3 fatty acid" includes a plurality of such fatty acids and reference to "the vitamin E isoform" includes reference to one or more vitamin E isoforms and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides dietary formulations comprising polyunsaturated fatty acids (PUFA) and vitamin E. A subject formulation is useful for treating various motor and communication disorders as well as allergic disorders. The present invention thus provides methods of treating such disorders, generally involving administering to an individual in need thereof an effective amount of a subject dietary formulation.

The present dietary formulations include a PUFA (e.g., an omega-3 fatty acid) and vitamin E in amounts and proportions that provide for treatment of the various categories of disorders mentioned above, including, e.g., apraxia. It has been found that such dietary formulations provide for a reduction in symptoms of various motor and communication disorders. Insights into a possible common mechanism contributed to the development of the subject formulations. While not wishing to be bound by theory, it is possible that dysregulation of fatty acid metabolism may play a central role in disorders such as apraxia, autism, and other disorders characterized at least in part by motor and/or communication dysfunction. In addition, it is possible that abnormal vitamin E bioavailability may play a role in these disorders. Furthermore, abnormal carnitine bioavailability may contribute to dysregulation of fatty acid metabolism on the cellular and mitochondrial level. Inflammation, oxidative stress and depletion of antioxidants such as glutathione in addition to vitamin E (vit E) may contribute to these disorders.

Formulations

As noted above, a subject dietary formulation comprises at least one polyunsaturated fatty acid (PUFA) and at least one vitamin E isoform. Suitable PUFA include, but are not limited to, omega-3 fatty acids and omega-6 fatty acids. Suitable omega-3 fatty acids include, e.g., α-linolenic acid (octadeca-9,12,15-trienoic acid), stearidonic acid (octadeca-6,9,12,15-tetraenoic acid), eicosapentaenoic acid (eicosa-5,8,11,14,17-pentaenoic acid; "EPA"), docosapentaenoic acid (docosa-7, 10,13,16,19-pentaenoic acid), eicosatetraenoic acid (eicosa-8,11,14,17-tetraenoic acid), and docosahexaenoic acid (docosa-4,7,10,13,16,19-hexaenoic acid; "DHA"). Suitable omega-6 fatty acids include, e.g., linoleic acid (9,12-octadecadienoic acid), γ-linolenic acid (6,9,12-octadecatrienoic acid; GLA), eicosadienoic acid (11,14-eicosadienoic acid), dihomo-γ-linolenic acid (8,11,14-eicosatrienoic acid), arachidonic acid (5,8,11,14-eicosatetraenoic acid), docosadienoic acid (13,16-docosadienoic acid), adrenic acid (7,10,13,16-docosatetraenoic acid), docosapentaenoic acid (4,7,10,13,16-docosapentaenoic acid), and calendic acid (8E,10E,12Z-octadecatrienoic acid).

A subject formulation can comprise one, two, three, four, five, six, seven, or eight different vitamin E isoforms. For example, in some embodiments, a subject formulation comprises α-tocopherol and γ-tocopherol; and substantially no other vitamin E isoforms. In other embodiments, a subject formulation includes α-tocopherol, γ-tocopherol, and at least one other vitamin E isoform. For example, in some embodiments, a subject formulation includes α-tocopherol, γ-tocopherol, and at least one of β-tocopherol, δ-tocopherol, α-tocotrienol, β-tocotrienol, γ-tocotrienol, and δ-tocotrienol. In other embodiments, a subject formulation includes α-tocopherol, γ-tocopherol, β-tocopherol, δ-tocopherol, α-tocotrienol, β-tocotrienol, γ-tocotrienol, and δ-tocotrienol.

In some embodiments, a subject formulation comprises at least one omega-3 fatty acid; and at least one vitamin E isoform. In some embodiments, a subject formulation comprises two different omega-3 fatty acids. In some embodiments, a subject formulation comprises eicosapentaenoic acid (EPA); docosohexaenoic acid (DHA); and at least one vitamin E isoform. In these embodiments, the ratio of EPA to DHA can range from about 1.5:1 (EPA:DHA) to about 5:1 (EPA:DHA), where the ratio is on a weight basis. For example, the EPA:DHA ratio can range from about 1.5:1 to about 2:1, from about 2:1 to about 2.5:1, from about 2.5:1 to about 3:1, from about 3:1 to about 3.5:1, from about 3.5:1 to about 4:1, from about 4:1 to about 4.5:1, or from about 4.5:1 to about 5:1. In some embodiments, the EPA:DHA ratio is 2.5:1.

In some embodiments, a subject formulation comprises at least two different omega-3 fatty acids; at least one vitamin E isoform; and at least one omega-6 fatty acid. For example, in some embodiments, a subject formulation comprises EPA; DHA; and at least one omega-6 fatty acid. In some embodiments, a subject formulation comprises EPA; DHA; at least one vitamin E isoform; and γ-linolenic acid (GLA). In some embodiments, a subject formulation comprises EPA; DHA; α-tocopherol; γ-tocopherol; and GLA.

In some embodiments, a subject formulation comprises at least two different omega-3 fatty acids; at least one vitamin E isoform; and an omega-9 fatty acid. In some embodiments, a subject formulation comprises at least two different omega-3 fatty acids; at least one vitamin E isoform; an omega-6 fatty acid; and an omega-9 fatty acid. The omega-9 fatty acid is in some embodiments a monounsaturated fatty acid. In other embodiments, the omega-9 fatty acid is a PUFA. In some embodiments, the omega-9 fatty acid is oleic acid.

Lipoic Acid

In some embodiments, a subject formulation further comprises α-lipoic acid. Thus, e.g., in some embodiments, a subject formulation comprises a PUFA; at least one vitamin E isoform; and α-lipoic acid. In some embodiments, a subject formulation comprises at least one omega-3 fatty acid; at least one vitamin E isoform; and α-lipoic acid. For example, in some embodiments, a subject formulation comprises EPA; DHA; at least one vitamin E isoform; and α-lipoic acid. In some embodiments, a subject formulation comprises EPA; DHA; α-tocopherol; γ-tocopherol; and α-lipoic acid. In other embodiments, a subject formulation comprises at least one omega-3 fatty acid; an omega-6 fatty acid; at least one vitamin E isoform; and α-lipoic acid. For example, in some embodiments, a subject formulation comprises EPA; DHA; GLA; α-tocopherol; γ-tocopherol; and α-lipoic acid.

The α-lipoic can exist as a 50/50 or racemic mixture of R-(+)-α-lipoic acid and S-(−)-α-lipoic acid. The α-lipoic acid ingredient of a subject formulation can be 100% R-(+) enantiomer. However, the α-lipoic acid can be present in a subject formulation in any mixture of the two enantiomers e.g. 10% S-(−) and 90% R-(+); 25% S-(−) and 75% R-(+); etc.

Carnitine

In some embodiments, a subject formulation further comprises carnitine. Thus, e.g., in some embodiments, a subject formulation comprises a PUFA; at least one vitamin E isoform; and carnitine. In some embodiments, a subject formulation comprises at least one omega-3 fatty acid; at least one vitamin E isoform; and carnitine. For example, in some embodiments, a subject formulation comprises EPA; DHA; at least one vitamin E isoform; and carnitine. In some embodiments, a subject formulation comprises EPA; DHA; α-tocopherol; γ-tocopherol; and carnitine. In other embodiments, a subject formulation comprises at least one omega-3 fatty acid; an omega-6 fatty acid; at least one vitamin E isoform; and carnitine. For example, in some embodiments, a subject formulation comprises EPA; DHA; GLA; α-tocopherol; γ-tocopherol; and carnitine. In other embodiments, a subject formulation comprises at least one omega-3 fatty acid; an omega-6 fatty acid; an omega-9 fatty acid; at least one vitamin E isoform; and carnitine. For example, in some embodiments, a subject formulation comprises EPA; DHA; GLA; oleic acid; α-tocopherol; γ-tocopherol; and carnitine.

In some embodiments, the carnitine component of a subject formulation is 90%-100% L-carnitine (or a salt thereof). In other embodiments, the carnitine component of a subject formulation is 90%-100% acetyl-carnitine. In other embodiments, the carnitine component of a subject formulation is a mixture of L-carnitine (or a salt thereof) and acetyl-carnitine. For example, in some embodiments, the carnitine component of a subject formulation can comprise 10% L-carnitine and 90% acetyl-carnitine; 15% L-carnitine and 85% acetyl-carnitine; 20% L-carnitine and 80% acetyl-carnitine; 25% L-carnitine and 75% acetyl-carnitine; 30% L-carnitine and 70% acetyl-carnitine; 40% L-carnitine and 60% acetyl-carnitine; 50% L-carnitine and 50% acetyl-carnitine; 60% L-carnitine and 40% acetyl-carnitine; 70% L-carnitine and 30% acetyl-carnitine; 75% L-carnitine and 25% acetyl-carnitine; 80% L-carnitine and 20% acetyl-carnitine; 85% L-carnitine and 15% acetyl-carnitine; or 90% L-carnitine and 10% acetyl-carnitine; or L-carnitine and acetyl-carnitine in any other proportion, where the percentages are by weight.

Amounts

The amounts in a subject formulation of PUFA and vitamin E, as well as the amounts of additional components such as carnitine and α-lipoic acid, can vary according to various factors, including, e.g., the age of the individual, the weight of the individual, the genetic makeup of the individual, and the severity of symptoms exhibited by the individual to whom a subject formulation is administered. The following are general guidelines. Amounts are given as per unit dose.

Where a subject formulation includes omega-3 fatty acids, the omega-3 fatty acids are present in amount of from about 100 mg to about 5000 mg, e.g., from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, from about 900 mg to about 1000 mg, from about 1000 mg to about 1100 mg, from about 1100 mg to about 1200 mg, from about 1200 mg to about 1300 mg, from about 1300 mg to about 1400 mg, from about 1400 mg to about 1500 mg, from about 1500 mg to about 1600 mg, from about 1600 mg to about 1700 mg, from about 1700 mg to about 1800 mg, from about 1800 mg to about 1900 mg, from about 1900 mg to about 2000 mg, from about 2000 mg to about 2500 mg, from about 2500 mg to about 3000 mg, from about 3000 mg to about 3500 mg, from about 3500 mg to about 4000 mg, from about 4000 mg to about 4500 mg, or from about 4500 mg to about 5000 mg per unit dose, where the amounts given are for individual omega-3 fatty acids or for total omega-3 fatty acids (e.g., where more than one omega-3 fatty acid is present).

For example, in some embodiments, a subject formulation comprises the omega-3 fatty acids EPA and DHA. In some embodiments, a subject formulation will comprise EPA in an amount of from about 500 mg to about 3000 mg, e.g., from about 500 mg to about 600 mg, from about 600 mg to about 700 mg, from about 700 mg to about 800 mg, from about 800 mg to about 900 mg, from about 900 mg to about 1000 mg, from about 1000 mg to about 1500 mg, from about 1500 mg to about 2000 mg, from about 2000 mg to about 2500 mg, or from about 2500 mg to about 3000 mg per unit dose; and will comprise DHA in an amount of from about 100 mg to about 400 mg, e.g., from about 100 mg to about 150 mg, from about 150 mg to about 200 mg, from about 200 mg to about 250 mg, from about 250 mg to about 300 mg, from about 300 mg to about 350 mg, or from about 350 mg to about 400 mg per unit dose.

Where a subject formulation comprises the omega-3 fatty acids EPA and DHA, the ratio of EPA to DHA can range from about 1.5:1 (EPA:DHA) to about 5:1 (EPA:DHA), where the ratio is on a weight basis. For example, the EPA:DHA ratio can range from about 1.5:1 to about 2:1, from about 2:1 to about 2.5:1, from about 2.5:1 to about 3:1, from about 3:1 to about 3.5:1, from about 3.5:1 to about 4:1, from about 4:1 to about 4.5:1, or from about 4.5:1 to about 5:1. In some embodiments, a subject formulation comprises EPA and DHA in a ratio of 2.5:1 EPA:DHA.

The amount of vitamin E present in a subject formulation can be expressed in units (International Units, or IU), or in milligrams. In the past, the U.S. Dietary Reference Intake (DRI) Recommended Dietary Allowances (RDA) of vitamin E were expressed in Units. This "units" term has been replaced in recent years by α-tocopherol equivalents ("α-TE") or milligrams. One Unit is equivalent to 1 mg of dl-α-tocopherol acetate or 0.6 mg d-α-tocopherol. Throughout this specification, amounts of vitamin E are given in mg.

The α-tocopherol and γ-tocopherol isoforms of vitamin E can be present in a subject formulation in an amount of from about 100 mg to about 10,000 mg, e.g., from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, from about 900 mg to about 1000 mg, from about 1000 mg to about 2000 mg, from about 2000 mg to about 3000 mg, from about 3000 mg to about 3000 mg, from about 4000 mg to about 5000 mg, from about 5000 mg to about 6000 mg, from about 6000 mg to about 7000 mg, from about 7000 mg to about 8000 mg, from about 8000 mg to about 9000 mg, or from about 9000 mg to about 10,000 mg per unit dose, where the amounts given are for individual isoforms of vitamin E. In some embodiments, the α-tocopherol is d-α-tocopherol.

In some embodiments, a subject formulation includes α-tocopherol in an amount of from about 500 mg to about 3000 mg per unit dose, e.g., in an amount of from about 500 mg, from about 500 mg to about 600 mg, from about 600 mg to about 700 mg, from about 700 mg to about 800 mg, from about 800 mg to about 900 mg, from about 900 mg to about 1000 mg, from about 1000 mg to about 2000 mg, or from about 2000 mg to about 3000 mg per unit dose; and γ-tocopherol in an amount of from about 200 mg to about 1000 mg per unit dose, e.g., in an amount of from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, or from about 900 mg to about 1000 mg per unit dose. In some of these embodiments, the formulation does not include vitamin E isoforms other than α-tocopherol and γ-tocopherol. In other embodiments, the formulation includes, in addition to α-tocopherol and γ-tocopherol, at least one additional vitamin E isoform.

In some embodiments, a subject formulation includes α-tocopherol and γ-tocopherol; and does not include other vitamin E isoforms. In other embodiments, a subject formulation includes α-tocopherol and γ-tocopherol; and one or more additional isoforms of vitamin E. Where a subject formulation includes α-tocopherol and γ-tocopherol, the α-tocopherol can be present in an amount of from about 500 mg to about 10,000 mg, e.g., from about 500 mg to about 1000 mg, from about 1000 mg to about 2000 mg, from about 2000 mg to about 3000 mg, from about 3000 mg to about 3000 mg, from about 4000 mg to about 5000 mg, from about 5000 mg to about 6000 mg, from about 6000 mg to about 7000 mg, from about 7000 mg to about 8000 mg, from about 8000 mg to about 9000 mg, or from about 9000 mg to about 10,000 mg; and the γ-tocopherol can be present in an amount of from about 100 mg to about 1000 mg, e.g., from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, or from about 900 mg to about 1000 mg per unit dose.

Other forms of vitamin E (e.g., β-tocopherol, δ-tocopherol, α-tocotrienol, β-tocotrienol, δ-tocotrienol, and γ-tocotrienol), if present in a subject formulation, can be present in an amount of from about 5 mg to about 2000 mg, e.g., from about 5 mg to about 10 mg, from about 10 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, or from about 175 mg to about 200 mg, from about 200 mg to about 250 mg, from about 250 mg to about 500 mg, from about 500 mg to about 750 mg, from about 750 mg to about 1000 mg, from about 1000 mg to about 1250 mg, from about 1250 mg to about 1500 mg, from about 1500 mg to about 1750 mg, or from about 1750 mg to about 2000 mg per unit dose, where the amounts given are for the individual isoforms of vitamin E.

Where a subject formulation comprises one or more omega-6 fatty acids, the omega-6 fatty acid can be present in the formulation in an amount of from about 50 mg to about 500 mg, e.g., from about 50 mg to about 75 mg, from about 75 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, or from about 450 mg to about 500 mg per unit dose.

Where a subject formulation comprises one or more omega-9 fatty acids, the omega-9 fatty acid can be present in a subject formulation in an amount of from about 50 mg to about 500 mg, e.g., from about 50 mg to about 75 mg, from about 75 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, or from about 450 mg to about 500 mg per unit dose.

Where a subject formulation comprises α-lipoic acid, the α-lipoic acid can be present in a subject formulation in an amount of from about 50 mg to about 1000 mg, e.g., from about 50 mg to about 75 mg, from about 75 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 600 mg, from about 600 mg to about 700 mg, from about 700 mg to about 800 mg, from about 800 mg to about 900 mg, or from about 900 mg to about 1000 mg per unit dose.

Where a subject formulation comprises carnitine, the carnitine can be present in a subject formulation in an amount of from about 150 mg to about 3000 mg, e.g., from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 600 mg, from about 600 mg to about 700 mg, from about 700 mg to about 800 mg, from about 800 mg to about 900 mg, from about 900 mg to about 1000 mg, from about 1000 mg to about 1250 mg, from about 1250 mg to about 1500 mg, from about 1500 mg to about 1750 mg, from about 1750 mg to about 2000 mg, from about 2000 mg to about 2250 mg, from about 2250 mg to about 2500 mg, from about 2500 mg to about 2750 mg, or from about 2750 mg to about 3000 mg per unit dose.

Additional Components

In some embodiments, a subject formulation includes, in addition to a PUFA and at least one vitamin E isoform, one or more additional components, e.g., one or more of: a) vitamin C (ascorbic acid); b) zinc; c) vitamin K; d) phosphocholine; e) coenzyme-Q; f) selenium; g) vitamin A; h) thiamin (vitamin $B_1$); i) riboflavin (vitamin $B_2$); j) pyridoxine, pyridoxamine, pyridoxine (collectively known as vitamin $B_6$); k) cyanocobalamin (vitamin $B_{12}$); l) vitamin D; m) arginine; n) calcium; o) magnesium; p) biotin (vitamin $B_7$); q) folic acid (vitamin $B_9$); r) pantothenic acid (vitamin $B_5$); s) tetrahydrobiopterin; and t) niacin or niacinamide (vitamin $B_3$). In some embodiments, a subject formulation includes a PUFA; at least one vitamin E isoform; and one, two, three, four, five, six, seven, eight, nine, ten, 11, 12, 13, 14, 15, 16, 17, 18, 19, or all twenty of: a) vitamin C (ascorbic acid); b) zinc; c) vitamin K; d) phosphocholine; e) coenzyme-Q; f) selenium; g) vitamin A; h) thiamin (vitamin $B_1$); i) riboflavin (vitamin $B_2$); j) pyridoxine, pyridoxamine, pyridoxine (collectively known as vitamin $B_6$); k) cyanocobalamin (vitamin $B_{12}$); l) vitamin D; m) arginine; n) calcium; o) magnesium; p) biotin (vitamin $B_7$); q) folic acid (vitamin $B_9$); r) pantothenic acid (vitamin $B_5$); s) tetrahydrobiopterin; and t) niacin or niacinamide (vitamin $B_3$). In some embodiments, a subject formulation includes one or more amino acids. In some embodiments, a subject formulation includes an antifungal agent (e.g., imidozoles and triazoles, nystatin, amphotericin B etc). In some embodiments, a subject formulation includes an anti-inflammatory agent. In some embodiments, a subject formulation includes an agent that reduces oxidative stress.

In some embodiments, a subject formulation includes a PUFA; at least one vitamin E isoform; and a pancreatic enzyme. In some embodiments, a subject formulation includes a PUFA; at least one vitamin E isoform; and a leukotriene inhibitor. In some embodiments, a subject formulation includes a PUFA; at least one vitamin E isoform; and a mast cell stabilizer (e.g., cromolyn). In other embodiments, a subject formulation includes a PUFA; at least one vitamin E isoform; a pancreatic enzyme; and a leukotriene inhibitor. For example, in some embodiments, a subject formulation includes an omega-3 fatty acid (e.g., EPA; DHA; or a combination of EPA and DHA, as described above; vitamin E (e.g., α-tocopherol and γ-tocopherol); α-lipoic acid; carnitine; a pancreatic enzyme; and a leukotriene inhibitor. Pancreatic enzymes and leukotriene inhibitors are described in more detail below.

Any minerals in a subject formulation can be present in salt form. Such salts can be any of the well known salts including carbonate, oxide, hydroxide, chloride, sulfate, phosphate, gluconate, lactate, acetate, fumarate, citrate, malate, amino acids, and the like for the cationic minerals and sodium, potassium, calcium, magnesium, and the like for the anionic minerals.

a) Vitamin C

In some embodiments, a subject formulation includes a PUFA (e.g., an omega-3 fatty acid and/or an omega-6 fatty acid); at least one isoform of vitamin E; and vitamin C. In some embodiments, a subject formulation includes a PUFA (e.g., an omega-3 fatty acid and/or an omega-6 fatty acid); at least one isoform of vitamin E; carnitine; and vitamin C. In other embodiments, a subject formulation includes a PUFA (e.g., an omega-3 fatty acid and/or an omega-6 fatty acid); at least one isoform of vitamin E; α-lipoic acid; and vitamin C.

"Vitamin C" includes all forms of ascorbic acid, such as L-ascorbic acid, D-ascorbic acid, DL-ascorbic acid, D-araboascorbic acid, dehydroascorbic acid, xyloascorbic acid, esters of ascorbic acid, salts of ascorbic acid, and the like.

Vitamin C can be present in a subject formulation in an amount of from about 80 mg to about 1000 mg, from about 80 mg to about 100 mg, from about 100 mg to about 200 mg, from about 200 mg to about 250 mg, from about 250 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, or from about 900 to about 1000 mg total daily dose or per unit dose.

b) Zinc

In some embodiments, a subject formulation includes a PUFA (e.g., an omega-3 fatty acid and/or an omega-6 fatty acid); at least one isoform of vitamin E; and zinc. In some embodiments, a subject formulation includes a PUFA (e.g., an omega-3 fatty acid and/or an omega-6 fatty acid); at least one isoform of vitamin E; carnitine; and zinc. In other embodiments, a subject formulation includes a PUFA (e.g., an omega-3 fatty acid and/or an omega-6 fatty acid); at least one isoform of vitamin E; α-lipoic acid; and zinc.

Zinc can be present in a subject formulation in the form of zinc gluconate, zinc sulfate, zinc chloride, or any salt of zinc. Zinc can be present in a subject formulation in an amount of from about 5 mg to about 50 mg, from about 5 mg to about 10 mg, from about 10 mg to about 15 mg, from about 15 mg to about 20 mg, from about 20 mg to about 25 mg, from about 25 mg to about 30 mg, from about 30 mg to about 40 mg, or from about 40 mg to about 50 mg total daily dose or per unit dose.

c) Vitamin K

In some embodiments, a subject formulation includes a PUFA (e.g., an omega-3 fatty acid and/or an omega-6 fatty acid); at least one isoform of vitamin E; and vitamin K. In some embodiments, a subject formulation includes a PUFA (e.g., an omega-3 fatty acid and/or an omega-6 fatty acid); at least one isoform of vitamin E; carnitine; and vitamin K. In other embodiments, a subject formulation includes a PUFA (e.g., an omega-3 fatty acid and/or an omega-6 fatty acid); at least one isoform of vitamin E; α-lipoic acid; and vitamin K.

"Vitamin K" includes Vitamin $K_1$ (phytonadione, phylloquinone, phytonactone); Vitamin $K_2$ (menaquinones, e.g., menaquinone-4, menaquinone-7, etc.); Vitamin $K_3$ (menadione; or 2-methyl-1,4-naphthoquinone); a salt of a vitamin K; and a derivative of a vitamin K. In some embodiments, a subject formulation includes vitamin $K_1$. In other embodiments, a subject formulation includes vitamin $K_2$. In other embodiments, a subject formulation includes vitamin $K_1$ and vitamin $K_2$.

Vitamin $K_1$ can be present in a subject formulation in an amount of from about 100 μg to about 10 mg (total daily dose), e.g., from about 100 μg to about 500 μg, from about 500 μg to about 1 mg, from about 1 mg to about 2.5 mg, from about 2.5 mg to about 5 mg, from about 5 mg to about 7.5 mg, or from about 7.5 mg to about 10 mg.

Vitamin $K_2$ can be present in a subject formulation in an amount of from about 100 μg to about 2 mg (total daily dose), e.g., from about 100 μg to about 250 μg, from about 250 μg to about 500 μg, from about 500 μg to about 750 μg, from about 750 μg to about 1 mg, from about 1 mg to about 1.25 mg, from about 1.25 mg to about 1.5 mg, from about 1.5 mg to about 1.75 mg, or from about 1.75 mg to about 2 mg.

In some embodiments, a subject formulation includes vitamin $K_1$. In other embodiments, a subject formulation includes vitamin $K_2$. In other embodiments, a subject formulation includes both vitamin $K_1$ and vitamin $K_2$.

d) Phosphocholine

In some embodiments, a subject formulation includes a PUFA (e.g., an omega-3 fatty acid and/or an omega-6 fatty acid); at least one isoform of vitamin E; and phosphocholine. In some embodiments, a subject formulation includes a PUFA (e.g., an omega-3 fatty acid and/or an omega-6 fatty acid); at least one isoform of vitamin E; carnitine; and phosphocholine. In other embodiments, a subject formulation includes a PUFA (e.g., an omega-3 fatty acid and/or an omega-6 fatty acid); at least one isoform of vitamin E; α-lipoic acid; and phosphocholine. "Phosphocholine" includes phosphatidylcholine derivatives of phosphocholine, e.g., polyenylphosphatidylcholine.

Phosphocholine (or a phosphatidylcholine such as polyenylphosphatidylcholine) can be present in a subject formulation in an amount of from about 500 mg to about 5000 mg, e.g., from about 500 mg to about 1000 mg, from about 1000 mg to about 2000 mg, from about 2000 mg to about 3000 mg, from about 3000 mg to about 4000 mg, or from about 4000 mg to about 5000 mg total daily dose or per unit dose.

e) Coenzyme Q

In some embodiments, a subject formulation includes a PUFA (e.g., an omega-3 fatty acid and/or an omega-6 fatty acid); at least one isoform of vitamin E; and Coenzyme Q. In some embodiments, a subject formulation includes a PUFA (e.g., an omega-3 fatty acid and/or an omega-6 fatty acid); at least one isoform of vitamin E; carnitine; and Coenzyme Q. In other embodiments, a subject formulation includes a PUFA (e.g., an omega-3 fatty acid and/or an omega-6 fatty acid); at least one isoform of vitamin E; α-lipoic acid; and Coenzyme Q.

"Coenzyme Q" (CoQ; 2,3-dimethoxy-5-methyl-6-polyprenyl-1,4-benzoquinone; also known as ubiquinone) refers to a group of lipid soluble benzoquinones involved in electron transport in mitochondrial preparations, e.g., in the oxidation of succinate or reduced nicotine adenine dinucleotide (NADH) via the cytochrome system. CoQ includes $CoQ_n$, where n is an integer from 1 to 12, and where n indicates the number of isoprenoid units. CoQ includes, e.g., $CoQ_{7\text{-}10}$, i.e. $CoQ_7$ (ubiquinone-7), $CoQ_9$ (ubiquinone-9), $CoQ_{10}$ (ubidecarenone), and mixtures of the foregoing. In some embodiments, the CoQ is ubidecarenone.

CoQ can be present in a subject formulation in an amount of from about 4 mg to about 250 mg, from about 4 mg to about 10 mg, from about 10 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 200 mg, or from about 200 mg to about 250 mg total daily dose or per unit dose.

f) Selenium

In some embodiments, a subject formulation includes a PUFA (e.g., an omega-3 fatty acid and/or an omega-6 fatty acid); at least one isoform of vitamin E; and selenium. In some embodiments, a subject formulation includes a PUFA (e.g., an omega-3 fatty acid and/or an omega-6 fatty acid); at least one isoform of vitamin E; carnitine; and selenium. In other embodiments, a subject formulation includes a PUFA (e.g., an omega-3 fatty acid and/or an omega-6 fatty acid); at least one isoform of vitamin E; α-lipoic acid; and selenium.

Selenium can be present in the form of sodium selenate, sodium selenite, selenomethionine, and the like. Selenium can be present in a subject formulation in an amount of from about 20 μg to about 500 μg, from about 20 μg to about 30 μg, from about 30 μg to about 40 μg, from about 40 μg to about 50 μg, from about 50 μg to about 75 μg, from about 75 μg to about 100 μg, from about 100 μg to about 150 μg, from about 150 μg to about 200 μg, from about 200 μg to about 250 μg, from about 250 μg to about 300 μg, from about 300 μg to about 350 μg, from about 350 μg to about 400 μg, or from about 400 μg to about 500 μg total daily dose.

g) Vitamin A

In some embodiments, a subject formulation includes a PUFA (e.g., an omega-3 fatty acid and/or an omega-6 fatty acid); at least one isoform of vitamin E; and vitamin A. In some embodiments, a subject formulation includes a PUFA (e.g., an omega-3 fatty acid and/or an omega-6 fatty acid); at least one isoform of vitamin E; carnitine; and vitamin A. In other embodiments, a subject formulation includes a PUFA (e.g., an omega-3 fatty acid and/or an omega-6 fatty acid); at least one isoform of vitamin E; α-lipoic acid; and vitamin A.

"Vitamin A" includes retinol, retinal (retinaldehyde), and retinoic acid; nor-retinoids; retro-retinoids; seco-retinoids (e.g., 1,6-seco-1,2-didehydroretinol); substituted retinoids (e.g., 5,6-Epoxy-5,6-dihydroretinol; ethyl 12-fluororetinoate; etc.); and analogs such as 3-hydroxyretinol, 3-hydroxyretinoic acid, 3-hydroxyretinal, 4-oxoretinol, 4-oxoretinoic acid, 4-oxoretinal, 3,4-didehydroretinol (vitamin $A_2$), 3,4-didehydroretinoic acid, 3,4-didehydroretinal, 4,5-didehydro-5,6-dihydroretinol, acycloretinol, acycloretinoic acid, and acycloretinal; and esters of vitamin A, e.g., an acetate ester, a succinate ester, a palmitate ester, etc.

Vitamin A can be present in a subject formulation in an amount of from about 200 IU to about 10,000 IU, e.g., 200 IU to about 250 IU, from about 250 IU to about 500 IU, from about 500 IU to about 1000 IU, from about 1000 IU to about 2000 IU, from about 2000 IU to about 3000 IU, from about 3000 IU to about 4000 IU, from about 4000 IU to about 5000 IU, from about 5000 IU to about 7500 IU, or from about 7500 IU to about 10,000 IU total daily dose.

h) Vitamin $B_1$

In some embodiments, a subject formulation includes a PUFA (e.g., an omega-3 fatty acid and/or an omega-6 fatty acid); at least one isoform of vitamin E; and vitamin $B_1$. In some embodiments, a subject formulation includes a PUFA (e.g., an omega-3 fatty acid and/or an omega-6 fatty acid); at least one isoform of vitamin E; carnitine; and vitamin $B_1$. In other embodiments, a subject formulation includes a PUFA (e.g., an omega-3 fatty acid and/or an omega-6 fatty acid); at least one isoform of vitamin E; α-lipoic acid; and vitamin $B_1$.

"Vitamin $B_1$" includes thiamine (also referred to as "thiamin"); the hydrochloride and nitrate salts of thiamine; and thiamine alkyl disulfides such as thiamine propyldisulfide, thiamine tetrahydrofurfuryl disulfide, and thiamine o-benzoyl disulfide; neopyrithiamine; oxyneopyrithiamine; and the like.

Vitamin $B_1$ can be present in a subject formulation in an amount of from about 0.05 mg to about 15 mg, from about 0.05 mg to about 0.1 mg, from about 0.1 mg to about 1.0 mg, from about 1.0 mg to about 1.5 mg, from about 1.5 mg to about 2.0 mg, from about 2.0 mg to about 2.5 mg, from about 2.5 mg to about 5 mg, from about 5 mg to about 7.5 mg, from about 7.5 mg to about 10 mg, from about 10 mg to about 12.5 mg, or from about 12.5 mg to about 15 mg total daily dose or per unit dose.

i) Vitamin $B_2$

In some embodiments, a subject formulation includes a PUFA (e.g., an omega-3 fatty acid and/or an omega-6 fatty acid); at least one isoform of vitamin E; and vitamin $B_2$. In some embodiments, a subject formulation includes a PUFA (e.g., an omega-3 fatty acid and/or an omega-6 fatty acid); at least one isoform of vitamin E; carnitine; and vitamin $B_2$. In other embodiments, a subject formulation includes a PUFA (e.g., an omega-3 fatty acid and/or an omega-6 fatty acid); at least one isoform of vitamin E; α-lipoic acid; and vitamin $B_2$.

"Vitamin $B_2$" includes riboflavin; crystalline riboflavin coenzyme forms of riboflavin such as flavin adenine dinucleotide, flavin adenine mononucleotide, riboflavin 5-phosphate and their salts. Vitamin $B_2$ can be present in a subject formulation in an amount of from about 0.05 mg to about 15 mg, from about 0.05 mg to about 0.1 mg, from about 0.1 mg to about 1.0 mg, from about 1.0 mg to about 1.5 mg, from about 1.5 mg to about 2.0 mg, from about 2.0 mg to about 2.5 mg, from about 2.5 mg to about 5 mg, from about 5 mg to about 7.5 mg, from about 7.5 mg to about 10 mg, from about 10 mg to about 12.5 mg, or from about 12.5 mg to about 15 mg total daily dose or per unit dose.

j) Vitamin $B_6$

In some embodiments, a subject formulation includes a PUFA (e.g., an omega-3 fatty acid and/or an omega-6 fatty acid); at least one isoform of vitamin E; and vitamin $B_6$. In some embodiments, a subject formulation includes a PUFA (e.g., an omega-3 fatty acid and/or an omega-6 fatty acid); at least one isoform of vitamin E; carnitine; and vitamin $B_6$. In other embodiments, a subject formulation includes a PUFA (e.g., an omega-3 fatty acid and/or an omega-6 fatty acid); at least one isoform of vitamin E; α-lipoic acid; and vitamin $B_6$.

"Vitamin $B_6$" includes pyridoxine, pyridoxal, pyridoxamine; and hydrochloride salts or 5-phosphates of pyridoxine, pyridoxamine, or pyridoxal. For example, pyridoxine hydrochloride can be included in a subject formulation.

Vitamin $B_6$ can be present in a subject formulation in an amount of from about 2 mg to about 250 mg, from about 2 mg to about 5 mg, from about 5 mg to about 10 mg, from about 10 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, or from about 225 mg to about 250 mg total daily dose or per unit dose.

k) Vitamin $B_{12}$

In some embodiments, a subject formulation includes a PUFA (e.g., an omega-3 fatty acid and/or an omega-6 fatty acid); at least one isoform of vitamin E; and vitamin $B_{12}$. In some embodiments, a subject formulation includes a PUFA (e.g., an omega-3 fatty acid and/or an omega-6 fatty acid); at least one isoform of vitamin E; carnitine; and vitamin $B_{12}$. In other embodiments, a subject formulation includes a PUFA (e.g., an omega-3 fatty acid and/or an omega-6 fatty acid); at least one isoform of vitamin E; α-lipoic acid; and vitamin $B_{12}$.

"Vitamin $B_{12}$" refers to vitamin $B_{12}$ (cyanocobalamin) and its pharmaceutical derivatives, such as hydroxocobalamin, cyano-10-chlorocobalamin, aquocobalamin perchlorate, aquo-10-chlorocobalamin perchlorate, azidocobalamin, chlorocobalamin, cobalamin, methylcobalamin, adenosylcobalamin, and hydroxocobalamin.

Vitamin $B_{12}$ can be present in a subject formulation in an amount of from about 2 µg to about 1000 µg, 2 µg to about 10 µg, from about 10 µg to about 25 µg, from about 25 µg to about 50 µg, from about 50 µg to about 100 µg, from about 100 µg to about 200 µg, from about 200 µg to about 300 µg, from about 300 µg to about 400 µg, from about 400 µg to about 500 µg, from about 500 µg to about 600 µg, from about 600 µg to about 700 µg, from about 700 µg to about 800 µg, from about 800 µg to about 900 µg, or from about 900 µg to about 1000 µg total daily dose or per unit dose.

l) Vitamin D

In some embodiments, a subject formulation includes a PUFA (e.g., an omega-3 fatty acid and/or an omega-6 fatty acid); at least one isoform of vitamin E; and vitamin D. In some embodiments, a subject formulation includes a PUFA (e.g., an omega-3 fatty acid and/or an omega-6 fatty acid); at least one isoform of vitamin E; carnitine; and vitamin D. In other embodiments, a subject formulation includes a PUFA (e.g., an omega-3 fatty acid and/or an omega-6 fatty acid); at least one isoform of vitamin E; α-lipoic acid; and vitamin D.

"Vitamin D" includes, e.g., cholecalciferol (D3), ergocalciferol (D2), and biologically active metabolites and precursors such as, e.g., 1-α-hydroxy Vitamin D, 25-hydroxy Vitamin D, 1,25-dihydroxy Vitamin D, and the like.

Vitamin D can be present in a subject formulation in an amount of from about 200 IU to about 800 IU, from about 200 IU to about 300 IU, from about 300 IU to about 400 IU, from about 400 IU to about 500 IU, from about 500 IU to about 600 IU, from about 600 IU to about 700 IU, or from about 700 IU to about 800 IU total daily dose or per unit dose.

m) Arginine

In some embodiments, a subject formulation includes a PUFA (e.g., an omega-3 fatty acid and/or an omega-6 fatty acid); at least one isoform of vitamin E; and arginine. In some embodiments, a subject formulation includes a PUFA (e.g., an omega-3 fatty acid and/or an omega-6 fatty acid); at least one isoform of vitamin E; carnitine; and arginine. In other embodiments, a subject formulation includes a PUFA (e.g., an omega-3 fatty acid and/or an omega-6 fatty acid); at least one isoform of vitamin E; α-lipoic acid; and arginine.

"Arginine" includes L-arginine, and arginine analogs such as methylated derivatives; and the like. Arginine (e.g., L-arginine) can be present in a subject formulation in an amount of from about 75 mg to about 9000 mg, from about 75 mg to about 100 mg, from about 100 mg to about 250 mg, from about 250 mg to about 500 mg, from about 500 mg to about 750 mg, from about 750 mg to about 1000 mg, from about 1000 mg to about 1500 mg, from about 1500 mg to about 2000 mg, from about 2000 mg to about 3000 mg, from about 3000 mg to about 4000 mg, from about 4000 mg to about 5000 mg, from about 5000 mg to about 6000 mg, from about 6000 mg to about 7000 mg, from about 7000 mg to about 8000 mg, or from about 8000 mg to about 9000 mg per unit dose.

n) Calcium

In some embodiments, a subject formulation includes a PUFA (e.g., an omega-3 fatty acid and/or an omega-6 fatty acid); at least one isoform of vitamin E; and calcium. In some embodiments, a subject formulation includes a PUFA (e.g., an omega-3 fatty acid and/or an omega-6 fatty acid); at least one isoform of vitamin E; carnitine; and calcium. In other embodiments, a subject formulation includes a PUFA (e.g., an omega-3 fatty acid and/or an omega-6 fatty acid); at least one isoform of vitamin E; α-lipoic acid; and calcium.

Calcium can be present in a subject formulation in the form of calcium carbonate, calcium citrate, calcium glubionate, calcium gluconate, calcium lactate, dibasic calcium phosphate, tribasic calcium phosphate, calcium acetate, and the like. Calcium can be present in a subject formulation in an amount of from about 40 mg to about 2000 mg, from about 40 mg to about 100 mg, from about 100 mg to about 250 mg, from about 250 mg to about 500 mg, from about 500 mg to about 750 mg, from about 750 mg to about 1000 mg, from about 1000 mg to about 1500 mg, or from about 1500 mg to about 2000 mg total daily dose or per unit dose.

o) Magnesium

In some embodiments, a subject formulation includes a PUFA (e.g., an omega-3 fatty acid and/or an omega-6 fatty acid); at least one isoform of vitamin E; and magnesium. In some embodiments, a subject formulation includes a PUFA (e.g., an omega-3 fatty acid and/or an omega-6 fatty acid); at least one isoform of vitamin E; carnitine; and magnesium. In other embodiments, a subject formulation includes a PUFA (e.g., an omega-3 fatty acid and/or an omega-6 fatty acid); at least one isoform of vitamin E; α-lipoic acid; and magnesium.

Magnesium can be present in a subject formulation as magnesium oxide, magnesium citrate, magnesium chloride, magnesium gluceptate, magnesium hydroxide, magnesium gluconate, magnesium lactate, magnesium pidolate, magnesium sulfate, and the like. Magnesium can be present in a subject formulation in an amount of from about 50 mg to about 450 mg, from about 50 mg to about 75 mg, from about 75 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, or from about 400 mg to about 450 mg total daily dose or per unit dose.

p) Vitamin $B_7$

In some embodiments, a subject formulation includes a PUFA (e.g., an omega-3 fatty acid and/or an omega-6 fatty acid); at least one isoform of vitamin E; and vitamin $B_7$. In some embodiments, a subject formulation includes a PUFA (e.g., an omega-3 fatty acid and/or an omega-6 fatty acid); at least one isoform of vitamin E; carnitine; and vitamin $B_7$. In other embodiments, a subject formulation includes a PUFA (e.g., an omega-3 fatty acid and/or an omega-6 fatty acid); at least one isoform of vitamin E; α-lipoic acid; and vitamin $B_7$.

"Vitamin $B_7$" includes biotin, oxybiotin, biocytin, biotinol, D-homobiotin, D-norbiotin, dethiobiotin, biotin sulfone, biotin diamine sulfate, and the like. Vitamin $B_7$ can be present in a subject formulation in an amount of from about 10 μg to about 800 μg, from about 10 μg to about 25 μg, from about 25 μg to about 50 μg, from about 50 μg to about 100 μg, from about 100 μg to about 200 μg, from about 200 μg to about 300 μg, from about 300 μg to about 400 μg, from about 400 μg to about 500 μg, from about 500 μg to about 600 μg, from about 600 μg to about 700 μg, or from about 700 μg to about 800 μg total daily dose or per unit dose.

q) Vitamin $B_9$

In some embodiments, a subject formulation includes a PUFA (e.g., an omega-3 fatty acid and/or an omega-6 fatty acid); at least one isoform of vitamin E; and vitamin $B_9$. In some embodiments, a subject formulation includes a PUFA (e.g., an omega-3 fatty acid and/or an omega-6 fatty acid); at least one isoform of vitamin E; carnitine; and vitamin $B_9$. In other embodiments, a subject formulation includes a PUFA (e.g., an omega-3 fatty acid and/or an omega-6 fatty acid); at least one isoform of vitamin E; α-lipoic acid; and vitamin $B_9$.

"Folic acid" (also known as pteroyl-L-glutamic acid; or vitamin $B_9$) includes folic acid and any chemical derivative of folic acid that function equivalently to folic acid, such as mono and polyglutamyl folates, dihydro and tetrahydro folates, methyl and formyl folates, and any isomer of a folate, e.g., an isomer of a reduced folate. Thus, e.g., "folic acid" includes dihydrofolic acid, tetrahydrofolic acid, 5-formyltetrahydrofolic acid, 10-formyltetrahydrofolic acid, 5-10 methylenetetrahydrofolic acid, 5-10 methenyltetrahydrofolic acid, 5-methyltetrahydrofolic acid, and derivatives of any of the foregoing; and a natural isomer of reduced folate, such as (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and polyglutamyl derivatives of any of the foregoing. Derivatives of folic acid include the precursors (pro-vitamins), metabolites, derivatives, and conjugates of the parent compound, any of which may be either naturally occurring or synthetic; as well as the salts of the compounds. "Folic acid" includes naturally occurring and synthetic forms of folic acid.

Folic acid can be present in a subject formulation in an amount of from about 200 µg to about 1000 µg, e.g., from about 200 µg to about 400 µg, from about 400 µg to about 500 µg, from about 500 µg to about 600 µg, from about 600 µg to about 700 µg, from about 700 µg to about 800 µg, from about 800 µg to about 900 µg, or from about 900 µg to about 1000 µg total daily dose or per unit dose.

r) Vitamin $B_5$

In some embodiments, a subject formulation includes a PUFA (e.g., an omega-3 fatty acid and/or an omega-6 fatty acid); at least one isoform of vitamin E; and vitamin $B_5$. In some embodiments, a subject formulation includes a PUFA (e.g., an omega-3 fatty acid and/or an omega-6 fatty acid); at least one isoform of vitamin E; carnitine; and vitamin $B_5$. In other embodiments, a subject formulation includes a PUFA (e.g., an omega-3 fatty acid and/or an omega-6 fatty acid); at least one isoform of vitamin E; α-lipoic acid; and vitamin $B_5$.

"Vitamin $B_5$" is also referred to as pantothenate or pantothenic acid, and encompasses salts such as calcium pantothenate; pantothenol; and panthenol. Vitamin $B_5$ can be present in a subject formulation in an amount of from about 0.4 mg to about 800 mg, from about 0.4 mg to about 1 mg, from about 1 mg to about 10 mg, from about 10 mg to about 25 mg, from about 25 mg to about 50 mg, from about 50 mg to about 100 mg, from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, or from about 700 mg to about 800 mg total daily dose or per unit dose.

s) Tetrahydrobiopterin

In some embodiments, a subject formulation includes a PUFA (e.g., an omega-3 fatty acid and/or an omega-6 fatty acid); at least one isoform of vitamin E; and tetrahydrobiopterin. In some embodiments, a subject formulation includes a PUFA (e.g., an omega-3 fatty acid and/or an omega-6 fatty acid); at least one isoform of vitamin E; carnitine; and tetrahydrobiopterin. In other embodiments, a subject formulation includes a PUFA (e.g., an omega-3 fatty acid and/or an omega-6 fatty acid); at least one isoform of vitamin E; α-lipoic acid; and tetrahydrobiopterin. In other embodiments, a subject formulation includes a PUFA (e.g., an omega-3 fatty acid and/or an omega-6 fatty acid); at least one isoform of vitamin E; α-lipoic acid; arginine; and tetrahydrobiopterin. In other embodiments, a subject formulation includes a PUFA (e.g., an omega-3 fatty acid and/or an omega-6 fatty acid); at least one isoform of vitamin E; α-lipoic acid; carnitine; and tetrahydrobiopterin. In other embodiments, a subject formulation includes a PUFA (e.g., an omega-3 fatty acid and/or an omega-6 fatty acid); at least one isoform of vitamin E; α-lipoic acid; arginine; carnitine; and tetrahydrobiopterin.

"Tetrahydrobiopterin" includes 5,6,7,8-tetrahydrobiopterin and salts thereof; L-erythro-5,6,7,8-tetrahydrobiopterin and salts thereof; and the like. Tetrahydrobiopterin can be present in a subject formulation in an amount of from about 20 mg to about 3000 mg, from about 20 mg to about 50 mg, from about 50 mg to about 100 mg, from about 100 mg to about 250 mg, from about 250 mg to about 500 mg, from about 500 mg to about 750 mg, from about 750 mg to about 1000 mg, from about 1000 mg to about 1500 mg, from about 1500 mg to about 2000 mg, from about 2000 mg to about 2500 mg, or from about 2500 mg to about 3000 mg.

t) Vitamin $B_3$

In some embodiments, a subject formulation includes a PUFA (e.g., an omega-3 fatty acid and/or an omega-6 fatty acid); at least one isoform of vitamin E; and vitamin $B_3$. In some embodiments, a subject formulation includes a PUFA (e.g., an omega-3 fatty acid and/or an omega-6 fatty acid); at least one isoform of vitamin E; carnitine; and vitamin $B_3$. In other embodiments, a subject formulation includes a PUFA (e.g., an omega-3 fatty acid and/or an omega-6 fatty acid); at least one isoform of vitamin E; α-lipoic acid; and vitamin $B_3$.

"Vitamin $B_3$" includes niacin, niacinamide, nicotinic acid, nicotinamide (niacinamide), the coenzyme forms of niacin such as nicotinamide adenine dinucleotide, and nicotinamide adenine dinucleotide phosphate. Vitamin $B_3$ can be present in a subject formulation in an amount of from about 0.5 mg to about 200 mg, from about 0.5 mg to about 1 mg, from about 1 mg to about 10 mg, from about 10 mg to about 25 mg, from about 25 mg to about 50 mg, from about 50 mg to about 75 mg, from about 75 mg to about 100 mg, from about 100 mg to about 150 mg, or from about 150 mg to about 200 mg.

Pancreatic Enzymes

As noted above, in some embodiments, a subject formulation comprises, in addition to a PUFA and at least one vitamin E isoform, a pancreatic enzyme.

Pancreatic enzymes include proteases, lipases, amylases, and nucleases. The term "pancreatic enzyme," as used herein, refers to any enzyme that provides a function (catalytic activity) of an enzyme produced by a human pancreas. For example, "pancreatic lipase" refers to any enzyme that provides a function of a lipase produced by a human pancreas.

In some embodiments, a subject formulation includes a lipase, e.g., a pancreatic lipase. In other embodiments, a subject formulation includes a pancreatic protease (e.g., trypsin, trypsinogen, chymotrypsin, chymotrypsinogen), and a pancreatic lipase. In other embodiments, a subject formation includes a pancreatic protease, a pancreatic lipase, and a pancreatic amylase.

In some embodiments, the enzyme is an inactive proenzyme (e.g., trypsinogen, chymotrysinogen). A pancreatic enzyme to be included in a subject formulation can be a naturally-occurring enzyme, a recombinant enzyme, or a synthetic enzyme; and can be from any of a variety of sources, e.g., a mammal, a fungus, a plant, etc. For example, fungal enzymes, and formulations comprising same, are described in, e.g., U.S. Pat. No. 6,051,220. In some embodiments, the enzyme is acid stable, e.g., is stable at a pH range of from about 2.8 to about 9. In some embodiments, the enzyme is in a microencapsulated and enteric coated formulation. Examples of such formulations include, e.g., Cotazym-S, Creon, Pancrease, Pancrease MT-16, Ultrase MT-20, and Zymase. Other suitable formulations include, e.g., a formulation as described in U.S. Pat. No. 5,750,104.

The amount of pancreatic enzyme present in a subject formulation can vary, according to need, and can be in a range of from about 2000 International Units (IU) to 40,000 IU per unit dose, e.g., from about 2000 IU to about 5000 IU, from about 5000 IU to about 7,500 IU, from about 7,500 IU to about 10,000 IU, from about 10,000 IU to about 15,000 IU, from about 15,000 IU to about 20,000 IU, from about 20,000 IU to about 30,000 IU, or from about 30,000 IU to about 40,000 IU per unit dose.

Leukotriene Inhibitors

As noted above, in some embodiments, a subject formulation comprises, in addition to a PUFA and at least one vitamin E isoform, a leukotriene inhibitor. Suitable leukotriene inhibitors include leukotriene receptor antagonists and leukotriene synthesis inhibitors. Exemplary leukotriene receptor antagonists include, e.g., zafirlukast (Accolate), montelukast (Singulair), pranlukast, iralukast, pobilukast and SKB-106,203. Leukotriene synthesis inhibitors include inhibitors of 5-lipoxygenase activity, where an exemplary 5-lipoxygenase inhibitor is zileuton (Zyflo). Suitable 5-lipoxygenase inhibitors include those described in, e.g., U.S. Pat. Nos. 5,364,877, 5,302,603, 5,234,950, 5,098,932 and 5,354,865. In some embodiments, a 5-lipoxygenase inhibitor also inhibits cyclooxygenase-2. In other embodiments, a 5-lipoxygenase inhibitor is a selective 5-lipoxygenase inhibitor, e.g., the inhibitor does not substantially inhibit enzymes other than 5-lipoxygenase, e.g., the inhibitor does not substantially inhibit a cyclooxygenase.

The amount of a leukotriene inhibitor that is included in a subject formulation can vary, depending on factors such as the age and/or weight of the individual to whom the formulation is administered, the severity of symptoms, etc. The amount of a leukotriene inhibitor that is included in a subject formulation can range from about 2 mg to about 100 mg, e.g., from about 2 mg to about 5 mg, from about 5 mg to about 10 mg, from about 10 mg to about 20 mg, from about 20 mg to about 30 mg, from about 30 mg to about 40 mg, from about 40 mg to about 50 mg, from about 50 mg to about 60 mg, from about 60 mg to about 70 mg, from about 70 mg to about 80 mg, from about 80 mg to about 90 mg, or from about 90 mg to about 100 mg per unit dose.

Amino Acids

In some embodiments, a subject formulation includes a PUFA; at least one vitamin E isoform; and one or more amino acids. For example, in some embodiments, a subject formulation includes arginine, glutamine, or both arginine and glutamine. If arginine and/or glutamine is present in a subject formulation, the arginine and/or glutamine is present in an amount of from about 500 mg to about 10 g per unit dose, e.g., from about 500 mg to about 750 mg, from about 750 mg to about 1 g, from about 1 g to about 2.5 g, from about 2.5 g to about 5 g, from about 5 g to about 7.5 g, or from about 7.5 g to about 10 g. For example, where a subject formulation includes a PUFA; at least one vitamin E isoform; and glutamine, the glutamine is present in an amount of from about 500 mg to about 10 g per unit dose, e.g., from about 500 mg to about 750 mg, from about 750 mg to about 1 g, from about 1 g to about 2.5 g, from about 2.5 g to about 5 g, from about 5 g to about 7.5 g, or from about 7.5 g to about 10 g. As another example, where a subject formulation includes a PUFA; at least one vitamin E isoform; and arginine, the arginine is present in an amount of from about 500 mg to about 10 g per unit dose, e.g., from about 500 mg to about 750 mg, from about 750 mg to about 1 g, from about 1 g to about 2.5 g, from about 2.5 g to about 5 g, from about 5 g to about 7.5 g, or from about 7.5 g to about 10 g. As another example, where a subject formulation includes a PUFA; at least one vitamin E isoform; and both arginine and glutamine, the arginine and glutamine are each present in an amount of from about 500 mg to about 10 g per unit dose, e.g., from about 500 mg to about 750 mg, from about 750 mg to about 1 g, from about 1 g to about 2.5 g, from about 2.5 g to about 5 g, from about 5 g to about 7.5 g, or from about 7.5 g to about 10 g.

Anti-fungal Agents

As noted above, in some embodiments, a subject formulation comprises, in addition to a PUFA and at least one vitamin E isoform, an anti-fungal agent. Suitable anti-fungal agents include, but are not limited to, nystatin, amphotericin B, clotrimazole, flucytosine, fluconazole, itraconazole, ketoconazole, and noxafil. Where the anti-fungal agent is nystatin, the nystatin can be present in a subject formulation in an amount of from about 100,000 Units (U) to about 800,000 U per unit dose, e.g., from about 100,000 U to about 200,000 U, from about 200,000 U to about 400,000 U, from about 400,000 U to about 600,000 U, or from about 600,000 U to about 800,000 U per unit dose. In some embodiments, a subject formulation comprises a PUFA, at least one vitamin E isoform (e.g., α-tocopherol and γ-tocopherol), carnitine, and nystatin.

Anti-inflammatory Agents

As noted above, in some embodiments, a subject formulation comprises, in addition to a PUFA and at least one vitamin E isoform, an anti-inflammatory agent. Suitable anti-inflammatory agents include, but are not limited to, steroidal anti-inflammatory agents, and non-steroidal anti-inflammatory agents. Suitable steroidal anti-inflammatory agents include, but are not limited to, hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, conisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures of two or more of the foregoing.

Suitable non-steroidal anti-inflammatory agents, include, but are not limited to, 1) the oxicams, such as piroxicam, isoxicam, tenoxicam, and sudoxicam; 2) the salicylates, such as aspirin, disalcid, benorylate, trilisate, safapryn, solprin, diflunisal, and fendosal; 3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac; 4) the fenamates, such as mefenamic, meclofenamic, flufenamic, niflumic, and tolfenamic acids; 5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone, mixtures of these non-steroidal anti-inflammatory agents may also be employed, as well as the pharmaceutically-acceptable salts and esters of these agents.

Anti-oxidants

As noted above, in some embodiments, a subject formulation comprises, in addition to a PUFA and at least one vitamin E isoform, an agent that reduces oxidative stress, e.g., an anti-oxidant. Suitable anti-oxidants include, but are not limited to, NXY-059 (Disufenton sodium); chain-breaking phenolic antioxidants (such as Vitamin E and butylated hydroxytoluene [BHT]); phenyl-substituted nitrones; azulenyl-substituted nitrones; α-phenyl-N-tert-butyl nitrone; stilbazulenyl nitrone (STAZN; Becker et al. (2002) *J. Am. Chem. Soc.* 124:4678); a spin-trap agent such as, e.g., N-t-butyl-a-phenylnitrone, 3,5-dibromo-4-nitrosobenzenesulfonic acid, 5,5-dimethyl-1-pyrroline N-oxide, 2-methyl-2-nitrosopropane, nitrosodisulfonic acid, a-(4-pyridyl-1-oxide)-N-t-butylnitrone, 3,3,5,5-tetramethylpyrroline N-oxide, 2,4,6-tri-t-butylnitrosobenzene, PTIYO (4-phenyl-2,2,5,5-tetramethyl imidazolin-1-yloxy-5-oxide), tempol (4-hydroxy 2,2,6,6-tetramethylpiperidine-1-oxyl); and the like. An anti-oxidant can be a nitrone anti-oxidant (e.g., STAZN), a polyphenol anti-oxidant, a flavonol anti-oxidant (e.g., baicalein), or a phenylpropanoid anti-oxidant (e.g., chlorogenic acid, fisetin, etc.). Also suitable is an anti-oxidant as described in U.S. Patent Publication No. 2007/0275932.

Additional Components

A subject formulation can include one or more additional components other than those listed above. Such additional components can include, e.g., pharmaceutically acceptable components such as lactose, glucose, sucrose, corn starch, potato starch, cellulose esters such as cellulose acetate, ethyl cellulose, magnesium stearate, calcium silicate, precipitated silica, talc, fatty acids such as stearic acid, microcrystalline cellulose, carnauba wax and the like. Diluents and other additives such as one or more pharmaceutically acceptable binding agents, fillers, supports, thickening agents, taste-improving agents, coloring agents, preservatives, stabilizers, regulators, emulsifiers, flow agents, absorbents, and the like or mixtures thereof may be used depending on the form of the composition employed.

Food-grade Components

In some embodiments, a subject formulation further includes one or more food-grade components. Suitable components include, but are not limited to, mono- and disaccharides; carbohydrates; proteins; amino acids; fatty acids; lipids; stabilizers; preservatives; flavoring agents; coloring agents; sweeteners; antioxidants, chelators, and carriers; texturants; pH adjusters; emulsifiers; stabilizers; soy and soy-based components; milk base solids; edible fibers; and the like. The food component can be isolated from a natural source, or can be synthesized. All components are food-grade components fit for human consumption.

Examples of suitable monosaccharides include sorbitol, mannitol, erythrose, threose, ribose, arabinose, xylose, ribulose, glucose, galactose, mannose, fructose, and sorbose. Non-limiting examples of suitable disaccharides include sucrose, maltose, lactitol, maltitol, maltulose, and lactose.

Suitable carbohydrates include oligosaccharides, polysaccharides, and/or carbohydrate derivatives. As used herein, the term "oligosaccharide" refers to a digestible linear molecule having from 3 to 9 monosaccharide units, wherein the units are covalently connected via glycosidic bonds. As used herein, the term "polysaccharide" refers to a digestible (i.e., capable of metabolism by the human body) macromolecule having greater than 9 monosaccharide units, wherein the units are covalently connected via glycosidic bonds. The polysaccharides may be linear chains or branched. Carbohydrate derivatives, such as a polyhydric alcohol (e.g., glycerol), may also be utilized as a complex carbohydrate herein. As used herein, the term "digestible" in the context of carbohydrates refers to carbohydrates that are capable of metabolism by enzymes produced by the human body. Examples of non-digestible carbohydrates are resistant starches (e.g., raw corn starches) and retrograded amyloses (e.g., high amylose corn starches). Non-limiting examples of suitable carbohydrates include raffinoses, stachyoses, maltotrioses, maltotetraoses, glycogens, amyloses, amylopectins, polydextroses, and maltodextrins.

Suitable starches include natural starches, e.g., starches derived from a natural source, such as those obtained from various plant species. Examples of plant sources of starch include, but are not limited to, corn, waxy corn, wheat, rice, tapioca, potato, pea and other sources known in the art. Suitable starches include modified starches. Modified starches are known in the art and the term generally refers to starch that has been physically or chemically altered to improve its functional characteristics. Suitable modified starches include, but are not limited to, pre-gelatinized starches, low viscosity starches (such as dextrins, acid-modified starches, oxidized starches and enzyme modified starches), derivatized starches, stabilized starches (such as starch esters and starch ethers), cross-linked starches, starch sugars (such as glucose syrup, dextrose and isoglucose) and starches that have been submitted to a combination of treatments (such as cross-linking and gelatinization) and mixtures thereof.

In some embodiments, a subject formulation that comprises one or more food components is gluten free. In some embodiments, a subject formulation that comprises one or more food components is casein free. In some embodiments, a subject formulation that comprises one or more food components is gluten free and casein free. "Gluten free" means that a subject formulation contains substantially no gluten; or, if the formulation does contain gluten, the gluten is present in an amount that does not induce an adverse reaction in an individual who is gluten sensitive (e.g., allergic to gluten) or who is gluten intolerant. Similarly, "casein free" means that a subject formulation contains substantially no gluten; or, if the formulation does contain gluten, the gluten is present in an amount that does not induce an adverse reaction in an individual who is casein sensitive (e.g., allergic to casein) or who is casein intolerant.

Suitable fats include, but are not limited to, triglycerides, including short-chain ($C_2$-$C_4$) and long-chain triglycerides ($C_{16}$-$C_{22}$).

Suitable texturants (also referred to as soluble fibers) include, but are not limited to, pectin (high ester, low ester); carrageenan; alginate (e.g., alginic acid, sodium alginate, potassium alginate, calcium alginate); guar gum; locust bean gum; psyllium; xanthan gum; gum arabic; fructo-oligosaccharides; inulin; agar; a modified cellulose gum; and functional blends of two or more of the foregoing.

Suitable modified cellulose gums include, for example, methylcellulose (MC), hydroxypropyl methylcellulose (HPMC), ethyl cellulose (EC), hydroxyethyl cellulose (HEC), hydroxypropylcellulose (HPC), hydroxypropyl methylcellulose acetate, hydroxyethyl methylcellulose, hydroxyethylcellulose acetate, hydroxyethyl ethylcellulose and combinations thereof.

Suitable emulsifiers include, but are not limited to, propylene glycol monostearate (PGMS), sodium stearoyl lactylate (SSL), calcium stearoyl lactylate (CSL), monoglycerides, diglycerides, monodiglycerides, polyglycerol esters, lactic acid esters, polysorbate, sucrose esters, diacetyl tartaric acid esters of mono-diglycerides (DATEM), citric acid esters of monoglycerides (CITREM) and combinations thereof. Additional suitable emulsifiers include DIMODAN, including DIMODAN™ B 727 and DIMODAN™ PV, GRINDSTED™ CITREM, GRINDSTED™ GA, GRINDSTED™ PS such as GRINDSTED™ PS 100, GRINDSTED™ PS 200, GRINDSTED™ PS 300, GRINDSTED™ PS 400; RYLO™ (manufactured and distributed by DANISCO CULTOR), including RYLO™ AC, RYLO™ CI, RYLO™ LA, RYLO™ MD, RYLO™ MG, RYLO™ PG, RYLO™ PR, RYLO™ SL, RYLO™ SO, RYLO™ TG; and combinations thereof.

Edible fibers include polysaccharides, oligosaccharides, lignin and associated plant substances. Suitable edible fibers include, but are not limited to, sugar beet fiber, apple fiber, pea fiber, wheat fiber, oat fiber, barley fiber, rye fiber, rice fiber, potato fiber, tomato fiber, other plant non-starch polysaccharide fiber, and combinations thereof.

Suitable flavoring agents include natural and synthetic flavors, "brown flavorings" (e.g., coffee, tea); dairy flavorings; fruit flavors; vanilla flavoring; essences; extracts; oleoresins; juice and drink concentrates; flavor building blocks (e.g., delta lactones, ketones); and the like; and combinations of such flavors. Examples of botanic flavors include, for example, tea (e.g., preferably black and green tea), aloe vera, guarana, ginseng, ginkgo, hawthorn, hibiscus, rose hips, chamomile, peppermint, fennel, ginger, licorice, lotus seed, schizandra, saw palmetto, sarsaparilla, safflower, St. John's Wort, curcuma, cardamom, nutmeg, cassia bark, buchu, cinnamon, jasmine, haw, chrysanthemum, water chestnut, sugar cane, lychee, bamboo shoots, vanilla, coffee, and the like.

Suitable sweeteners include, but are not limited to, alitame; dextrose; fructose; lactilol; polydextrose; xylitol; xylose; aspartame, saccharine, cyclamates, acesulfame K, L-aspartyl-L-phenylalanine lower alkyl ester sweeteners, L-aspartyl-D-alanine amides; L-aspartyl-D-serine amides; L-aspartyl-hydroxymethyl alkane amide sweeteners; L-aspartyl-1-hydroxyethylalkane amide sweeteners; and the like.

Suitable anti-oxidants include, but are not limited to, tocopherols (natural, synthetic); ascorbyl palmitate; gallates; butylated hydroxyanisole (BHA); butylated hydroxytoluene (BHT); tert-butyl hydroquinone (TBHQ); and the like.

Suitable coloring agents include, but are not limited to, FD&C dyes (e.g., yellow #5, blue #2,red #40), FD&C lakes; Riboflavin; β-carotene; natural coloring agents, including, for example, fruit, vegetable, and/or plant extracts such as grape, black currant, aronia, carrot, beetroot, red cabbage, and hibiscus.

Exemplary preservatives include sorbate, benzoate, and polyphosphate preservatives.

Suitable emulsifiers include, but are not limited to, diglycerides; monoglycerides; acetic acid esters of mono- and diglycerides; diacetyl tartaric acid esters of mono- and diglycerides; citric acid esters of mono- and diglycerides; lactic acid esters of mono- and diglycerides; fatty acids; polyglycerol esters of fatty acids; propylene glycol esters of fatty acids; sorbitan monostearates; sorbitan tristearates; sodium stearoyl lactylates; calcium stearoyl lactylates; and the like.

Suitable agents for pH adjustment include organic as well as inorganic edible acids. The acids can be present in their undissociated form or, alternatively, as their respective salts, for example, potassium or sodium hydrogen phosphate, potassium or sodium dihydrogen phosphate salts. Exemplary acids are edible organic acids which include citric acid, malic acid, fumaric acid, adipic acid, phosphoric acid, gluconic acid, tartaric acid, ascorbic acid, acetic acid, phosphoric acid and mixtures thereof.

Food Formulations

A subject formulation can be prepared in a variety of ways for consumption by an individual, and, as indicated above, can include one or more food components. Food formulations can be in a variety of forms, including powders; liquids; gels; and solid forms such as bars, tablets, capsules, candies, etc. Formulations of interest include foods for veterinary or human use, including food bars (e.g. cereal bars, breakfast bars, energy bars, nutritional bars); drinks; fortified drinks; carbonated beverages; drink supplements (e.g., powders to be added to a drink); powders to be mixed with food; tablets; lozenges; candy; candy-like formulations, e.g., chewable gel formulations, e.g., chewable gel candy in the shape of an animal; puddings; and the like. Suitable food formulations also include those described in U.S. Pat. No. 7,067,150.

A food product can have final moisture content between about 0% and about 100%, e.g., from about 0% to about 1%, from about 1% to about 5%, from about 5% to about 10%, from about 10% to about 30%, from about 30% to about 50%, from about 50% to about 80%, or from about 80% to about 100%.

Packages

The present invention further provides a package comprising a subject formulation. In some embodiments, a subject package comprises a single dosage form of a subject formulation. In other embodiments, a subject package a subject package comprising multiple (e.g., 2, 3, 4, 5, 6, 7, 8, 9, 10, or more) dosage forms of a subject formulation.

As one non-limiting example, a subject food product can be packaged in such a way that multiple doses are contained in a single package, optionally where individual unit dosage forms are separated in individual compartments in a single package. The dosage forms can be in a variety of forms, e.g., tablets or lozenges that are palatable (e.g., flavored so as to be palatable, such as with fruit flavorings, sugars, and the like, as discussed above). Unit dosage forms include tablets, capsules, lozenges, candies, bars, a unit of powder (e.g., 1 tablespoon of a powder; a unit of a liquid, (e.g., a 1 tablespoon of a liquid), etc.

A subject package in some embodiments will further include instructions for use, including e.g., dosage amounts and dosage frequencies. Instructions are in some embodiments printed directly on the package. In other embodiments, instructions are printed material provided as a package insert. Instructions can also be provided in other media, e.g., electronically in digital or analog form, e.g., on an audio cassette, an audio tape, a compact disc, a digital versatile disk, and the like.

EXEMPLARY FORMULATIONS

The following are exemplary formulations. As noted above, in addition to the components specifically listed below, a subject formulation can include one or more additional active and/or inactive components, food-grade components, etc. In the exemplary formulations below, amounts are given as per unit dose.

Exemplary Formulation 1

| Component | Amount |
| --- | --- |
| EPA | 700 mg |
| DHA | 250 mg |

-continued

| Component | Amount |
|---|---|
| α-tocopherol | 500 mg |
| γ-tocopherol | 200 mg |

Exemplary Formulation 2

| Component | Amount |
|---|---|
| EPA | 700 mg |
| DHA | 250 mg |
| α-tocopherol | 1500 mg |
| γ-tocopherol | 600 mg |

In some embodiments, the amount of α-tocopherol in Exemplary formulation 1 is increased to from 1000 mg to 3000 mg. In some embodiments, the amount of γ-tocopherol in Exemplary formulation 1 is increased to from 500 mg to 1000 mg.

In some embodiments, the amount of α-tocopherol in Exemplary formulation 2 is increased to from 1000 mg to 3000 mg. In some embodiments, the amount of γ-tocopherol in Exemplary formulation 2 is increased to from 500 mg to 1000 mg.

In some embodiments, a subject formulation will include α-lipoic acid and/or carnitine.

Exemplary Formulation 3

| Component | Amount |
|---|---|
| EPA | 700 mg |
| DHA | 250 mg |
| α-tocopherol | 500 mg |
| γ-tocopherol | 200 mg |
| α-lipoic acid | 100 mg |

Exemplary Formulation 4

| Component | Amount |
|---|---|
| EPA | 700 mg |
| DHA | 250 mg |
| α-tocopherol | 1500 mg |
| γ-tocopherol | 600 mg |
| α-lipoic acid | 600 mg |

Exemplary Formulation 5

| Component | Amount |
|---|---|
| EPA | 700 mg |
| DHA | 165 mg |
| α-tocopherol | 500 mg |
| γ-tocopherol | 200 mg |
| carnitine | 200 mg |

Exemplary Formulation 6

| Component | Amount |
|---|---|
| EPA | 700 mg |
| DHA | 250 mg |
| α-tocopherol | 1500 mg |
| γ-tocopherol | 600 mg |
| carnitine | 3000 mg |

In some embodiments, the amount of α-tocopherol in any one of Exemplary formulations 3-6 is increased to from 1000 mg to 3000 mg. In some embodiments, the amount of γ-tocopherol in any one of Exemplary formulations 3-6 is increased to from 500 mg to 1000 mg.

In some embodiments, a subject formulation will include an omega-6 fatty acid.

Exemplary Formulation 7

| Component | Amount |
|---|---|
| EPA | 700 mg |
| DHA | 250 mg |
| GLA | 70 mg |
| α-tocopherol | 500 mg |
| γ-tocopherol | 200 mg |

Exemplary Formulation 8

| Component | Amount |
|---|---|
| EPA | 700 mg |
| DHA | 250 mg |
| GLA | 70 mg |
| α-tocopherol | 1500 mg |
| γ-tocopherol | 600 mg |

In some embodiments, a subject formulation will include an omega-9 fatty acid.

Exemplary Formulation 9

| Component | Amount |
|---|---|
| EPA | 700 mg |
| DHA | 250 mg |
| GLA | 70 mg |
| Oleic acid | 250 mg |
| α-tocopherol | 500 mg |
| γ-tocopherol | 200 mg |

Exemplary Formulation 10

| Component | Amount |
|---|---|
| EPA | 700 mg |
| DHA | 250 mg |
| GLA | 70 mg |

-continued

| Component | Amount |
|---|---|
| Oleic acid | 250 mg |
| α-tocopherol | 1500 mg |
| γ-tocopherol | 600 mg |

Exemplary Formulation 11

| Component | Amount |
|---|---|
| EPA | 700 mg |
| DHA | 250 mg |
| GLA | 70 mg |
| Oleic acid | 250 mg |
| α-tocopherol | 500 mg |
| γ-tocopherol | 200 mg |
| α-lipoic acid | 100 mg |

Exemplary Formulation 12

| Component | Amount |
|---|---|
| EPA | 700 mg |
| DHA | 250 mg |
| GLA | 70 mg |
| Oleic acid | 250 mg |
| α-tocopherol | 1500 mg |
| γ-tocopherol | 600 mg |
| α-lipoic acid | 600 mg |

Exemplary Formulation 13

| Component | Amount |
|---|---|
| EPA | 700 mg |
| DHA | 250 mg |
| GLA | 70 mg |
| Oleic acid | 250 mg |
| α-tocopherol | 500 mg |
| γ-tocopherol | 200 mg |
| α-lipoic acid | 100 mg |
| Carnitine | 200 mg |

Exemplary Formulation 14

| Component | Amount |
|---|---|
| EPA | 700 mg |
| DHA | 250 mg |
| GLA | 70 mg |
| Oleic acid | 250 mg |
| α-tocopherol | 1500 mg |
| γ-tocopherol | 600 mg |
| α-lipoic acid | 600 mg |
| Carnitine | 3000 mg |

Exemplary Formulation 15

| Component | Amount |
|---|---|
| EPA | 700 mg |
| DHA | 250 mg |
| GLA | 70 mg |
| Oleic acid | 200 mg |
| α-tocopherol | 500 mg |
| γ-tocopherol | 200 mg |
| α-lipoic acid | 100 mg |
| Carnitine | 1000 mg |

Exemplary Formulation 16

| Component | Amount |
|---|---|
| EPA | 700 mg |
| DHA | 250 mg |
| GLA | 70 mg |
| Oleic acid | 250 mg |
| α-tocopherol | 1500 mg |
| γ-tocopherol | 600 mg |
| α-lipoic acid | 200 mg |
| Carnitine | 3000 mg |

In some embodiments, a subject formulation includes one or more of vitamin C, phosphocholine, zinc, and vitamin K. For example, exemplary formulations include the following.

Exemplary Formulation 17

| Component | Amount |
|---|---|
| EPA | 700 mg |
| DHA | 250 mg |
| GLA | 70 mg |
| Oleic acid | 250 mg |
| α-tocopherol | 500 mg |
| γ-tocopherol | 200 mg |
| α-lipoic acid | 100 mg |
| Carnitine | 1000 mg |
| Vitamin C | 250 mg |

Exemplary Formulation 18

| Component | Amount |
|---|---|
| EPA | 700 mg |
| DHA | 250 mg |
| GLA | 70 mg |
| Oleic acid | 250 mg |
| α-tocopherol | 1500 mg |
| γ-tocopherol | 600 mg |
| α-lipoic acid | 600 mg |
| Carnitine | 3000 mg |
| Vitamin C | 500 mg |

Exemplary Formulation 19

| Component | Amount |
|---|---|
| EPA | 700 mg |
| DHA | 250 mg |
| GLA | 70 mg |
| Oleic acid | 250 mg |
| α-tocopherol | 500 mg |
| γ-tocopherol | 200 mg |
| α-lipoic acid | 100 mg |
| Carnitine | 200 mg |
| Vitamin C | 250 mg |
| Phosphocholine | 1 g |

Exemplary Formulation 20

| Component | Amount |
|---|---|
| EPA | 700 mg |
| DHA | 250 mg |
| GLA | 70 mg |
| Oleic acid | 250 mg |
| α-tocopherol | 1500 mg |
| γ-tocopherol | 600 mg |
| α-lipoic acid | 600 mg |
| Carnitine | 3000 mg |
| Vitamin C | 500 mg |
| Phosphocholine | 3 g |

Exemplary Formulation 21

| Component | Amount |
|---|---|
| EPA | 700 mg |
| DHA | 250 mg |
| GLA | 70 mg |
| Oleic acid | 250 mg |
| α-tocopherol | 500 mg |
| γ-tocopherol | 200 mg |
| α-lipoic acid | 100 mg |
| Carnitine | 200 mg |
| Vitamin C | 250 mg |
| Phosphocholine | 1 g |
| Zinc | 15 mg |

Exemplary Formulation 22

| Component | Amount |
|---|---|
| EPA | 700 mg |
| DHA | 250 mg |
| GLA | 70 mg |
| Oleic acid | 250 mg |
| α-tocopherol | 1500 mg |
| γ-tocopherol | 600 mg |
| α-lipoic acid | 600 mg |
| Carnitine | 3000 mg |
| Vitamin C | 500 mg |
| Phosphocholine | 3 g |
| Zinc | 30 mg |

Exemplary Formulation 23

| Component | Amount |
|---|---|
| EPA | 700 mg |
| DHA | 250 mg |
| GLA | 70 mg |
| Oleic acid | 250 mg |
| α-tocopherol | 500 mg |
| γ-tocopherol | 200 mg |
| α-lipoic acid | 100 mg |
| Carnitine | 200 mg |
| Vitamin C | 250 mg |
| Phosphocholine | 1 g |
| Zinc | 15 mg |
| Vitamin K | 5 μg |

Exemplary Formulation 24

| Component | Amount |
|---|---|
| EPA | 700 mg |
| DHA | 250 mg |
| GLA | 70 mg |
| Oleic acid | 250 mg |
| α-tocopherol | 1500 mg |
| γ-tocopherol | 600 mg |
| α-lipoic acid | 600 mg |
| Carnitine | 3000 mg |
| Vitamin C | 500 mg |
| Phosphocholine | 3 g |
| Zinc | 30 mg |
| Vitamin K (K1 + K2) | 10 mg |

Exemplary Formulation 25

| Component | Amount |
|---|---|
| EPA | 700 mg |
| DHA | 250 mg |
| GLA | 70 mg |
| Oleic acid | 200 mg |
| α-tocopherol | 500 mg |
| γ-tocopherol | 200 mg |
| α-lipoic acid | 100 mg |
| Carnitine | 500 mg |
| Vitamin C | 100 mg |
| Phosphocholine | 1 g |
| Zinc | 5 mg |
| Vitamin K1 | 3 mg |
| Vitamin K2 | 350 μg |

Exemplary Formulation 26

| Component | Amount |
|---|---|
| EPA | 700 mg |
| DHA | 250 mg |
| GLA | 70 mg |
| Oleic acid | 200 mg |
| α-tocopherol | 1500 mg |
| γ-tocopherol | 500 mg |
| α-lipoic acid | 200 mg |
| Carnitine | 2000 mg |
| Vitamin C | 500 mg |

-continued

| Component | Amount |
| --- | --- |
| Phosphocholine | 3 g |
| Zinc | 15 mg |
| Vitamin K1 | 10 mg |
| Vitamin K2 | 1 mg |

Exemplary Formulation 27

| Component | Amount |
| --- | --- |
| EPA | 700 mg |
| DHA | 250 mg |
| GLA | 70 mg |
| Oleic acid | 200 mg |
| α-tocopherol | 1500 mg |
| γ-tocopherol | 500 mg |
| α-lipoic acid | 200 mg |
| Carnitine | 2000 mg |
| Vitamin C | 500 mg |
| Phosphocholine | 3 g |
| Zinc | 15 mg |
| Vitamin $K_1$ | 10 mg |
| Vitamin $K_2$ | 1 mg |
| arginine | 3000 mg |
| Co-enzyme Q | 200 mg |
| Selenium | 50 μg |
| Vitamin A | 3000 IU |
| Thiamin (B1) | 7.5 mg |
| Riboflavin (B2) | 7.5 mg |
| Vitamin B6 | 200 mg |
| Vitamin B12 | 1 mg |
| Vitamin D | 400 IU |
| Calcium | 100 mg elemental |
| magnesium | 200 mg |
| Biotin (B7) | 50 μg |
| Folic acid | 400 μg |
| Pantothenic acid | 10 mg |
| tetrahydrobiopterin | 50 mg |
| Niacin | 15 mg |

A subject formulation can be prepared as a single dosage form, or divided into two or more dosage forms. A subject formulation can comprise one unit dose; two unit doses; three unit doses; or more than three unit doses. For example, any of exemplary formulations 1-27 can be divided into two or more capsules, two or more tablets, two or more bars, two or more units of a powder (e.g., two or more grams of a powder, two or more tablespoons of a powder, etc.), two or more units liquid (e.g., two or more 1-ml units of a liquid, two or more 5-ml units of a liquid, etc.), two or more chewable gel units, or two or more units of another dosage form. Alternatively, a subject formulation can be a liquid formulation, where it can be formulated in a single dose (e.g., 1-15 ml) or formulated such that it is administered in two or more doses, where each dose is 1-10 ml). For example, exemplary formulations 1-27 provide the unit doses of the various components, which can be administered to an individual in one, two, three, four, or more, doses, which doses can be in various dosage forms, e.g., tablets, capsules, liquids, powders, food products, etc.

Treatment Methods

The present invention provides methods of treating various disorders, involving administering to an individual in need thereof an effective amount of a subject formulation. A subject method is useful for treating various disorders, including, but not limited to, apraxia, dyspraxia, autism, autism spectrum disorder, attention deficit/hyperactivity disorder, dyslexia, depression, sensory integration dysfunction; immune system disorders such as celiac disease, sprue, gluten sensitivity, a malabsorption syndrome, asthma, food allergy, leaky gut syndrome, and eczema; cardiovascular disease; diabetes; and inflammatory conditions such as rheumatoid arthritis.

A subject formulation is in some embodiments administered to an individual with apraxia, to treat the apraxia. In these embodiments, an effective amount of a subject formulation is an amount that, when administered in one or more doses, is effective to provide for an improvement in one or more of an oral movement score, a simple phonemic/syllabic score, a complex phonemic/syllabic score, and a spontaneous length and complexity score, e.g., in the Kaufman Praxis Test. For example, an effective amount of a subject formulation is an amount that, when administered in one or more doses, is effective to provide for an increase in percentile score of from about 5 to about 10 percentile, from about 10 to about 20 percentile, from about 20 to about 40 percentile, from about 40 to about 60 percentile, from about 60 to about 70 percentile, or from about 70 to about 90 percentile, on one or more of an oral movement score, a simple phonemic/syllabic score, a complex phonemic/syllabic score, and a spontaneous length and complexity score, e.g., in the Kaufman Praxis Test. Whether a subject formulation is effective in treating a disorder such as apraxia can be determined using well-established tests, such as the Kaufman Praxis Test.

A subject formulation is in some embodiments administered to an individual with an immune system disorder, to treat the immune system disorder. In these embodiments, an effective amount of a subject formulation is an amount that, when administered in one or more doses, is effective to provide for a reduction in one or more symptoms of an immune system disorder. For example, where the immune system disorder is an allergic disorder, an effective amount of a subject formulation is an amount that, when administered in one or more doses, is effective to provide for a reduction in circulating factor that is an indicator of an allergic disorder of from about 10% to about 20%, from about 20% to about 25%, from about 25% to about 30%, from about 30% to about 40%, from about 40% to about 50%, from about 50% to about 60%, from about 60% to about 70%, or from about 70% to about 80%, or more, of the level of the circulating factor present following exposure to an allergy-stimulating allergen. Circulating factors that are indicators of an allergic disorder include, e.g., allergen-specific IgE; inflammatory biomarkers; C-reactive protein; cytokines that are indicative of a Th2 immune response; and the like. As another example, where the immune system disorder is an allergic disorder, an effective amount of a subject formulation is an amount that, when administered in one or more doses, is effective to provide for one or more of: i) clinical improvement in one or more of sneezing, wheezing, runny nose, and other symptoms of an allergic reaction; ii) decreased number of visits to a medical personnel for treatment for the allergic disorder; and iii) decreased use of medications used to treat the symptoms of an allergic disorder. Whether a subject formulation is effective in treating an immune system disorder such as an allergic disorder can be determined using any well-established test, e.g., immunoassays for measuring IgE levels (e.g., allergen-specific IgE levels), and the like.

A subject formulation is administered, e.g., orally, to an individual in need thereof in any frequency deemed appropriate to treat the condition or disorder. For example, a subject formulation can be administered three times daily, twice daily, once daily, every other day, three times per week, twice per week, once per week, or less often. In some embodiments, a subject formulation is administered daily. In other embodiments, a subject formulation is administered every other day. For example, a unit dose of a subject formulation can be administered once, twice, or three times daily.

A subject formulation can be administered at any frequency, as discussed above, over any period of time, as necessary to treat the condition or disorder. Thus, a subject formulation can be administered over a period of time of from about one week to about one month, from about one month to about three months, from about three months to about 6 months, from about 6 months to about one year, from about one year to about three years, from about three years to about six years, from about six years to about 10 years, or more than 10 years.

The dosages of PUFA and vitamin E, as well as the dosages of additional components such as carnitine and α-lipoic acid, can vary according to various factors, including, e.g., the age of the individual, the weight of the individual, the genetic makeup of the individual, and the severity of symptoms exhibited by the individual to whom a subject formulation is administered. The following are general guidelines.

Where a subject formulation includes omega-3 fatty acids, the dosage of the omega-3 fatty acids ranges from about 100 mg/day to about 5000 mg/day, e.g., from about 100 mg/day to about 200 mg/day, from about 200 mg/day to about 300 mg/day, from about 300 mg/day to about 400 mg/day, from about 400 mg/day to about 500 mg/day, from about 500 mg/day to about 600 mg/day, from about 600 mg/day to about 700 mg/day, from about 700 mg/day to about 800 mg/day, from about 800 mg/day to about 900 mg/day, from about 900 mg/day to about 1000 mg/day, from about 1000 mg/day to about 1100 mg/day, from about 1100 mg/day to about 1200 mg/day, from about 1200 mg/day to about 1300 mg/day, from about 1300 mg/day to about 1400 mg/day, from about 1400 mg/day to about 1500 mg/day, from about 1500 mg/day to about 2000 mg/day, from about 2000 mg/day to about 3000 mg/day, from about 3000 mg/day to about 4000 mg/day, or from about 4000 mg/day to about 5000 mg/day, where the dosages given are for individual omega-3 fatty acids or for total omega-3 fatty acids (e.g., where more than one omega-3 fatty acid is present).

For example, in some embodiments, a subject formulation comprises the omega-3 fatty acids EPA and DHA. In some embodiments, the dosage for EPA will range from about 500 mg/day to about 3000 mg/day, e.g., from about 500 mg/day to about 600 mg/day, from about 600 mg/day to about 700 mg/day, from about 700 mg/day to about 800 mg/day, from about 800 mg/day to about 900 mg/day, or from about 900 mg/day to about 1000 mg/day; and the dosage of DHA will range from about 100 mg/day to about 1000 mg/day, e.g., from about 100 mg/day to about 150 mg/day, from about 150 mg/day to about 200 mg/day, from about 200 mg/day to about 250 mg/day, from about 250 mg/day to about 300 mg/day, from about 300 mg/day to about 350 mg/day, from about 350 mg/day to about 400 mg/day, from about 400 mg/day to about 500 mg/day, from about 500 mg/day to about 600 mg/day, from about 600 mg/day to about 700 mg/day, from about 700 mg/day to about 800 mg/day, from about 800 mg/day to about 900 mg/day, or from about 900 mg/day to about 1000 mg/day.

The dosage of α-tocopherol ranges from about 10 mg/kg/day to about 200 mg/kg/day, e.g., from about 10 mg/kg/day to about 25 mg/kg/day, from about 25 mg/kg/day to about 50 mg/kg/day, from about 50 mg/kg/day to about 75 mg/kg/day, from about 75 mg/kg/day to about 100 mg/kg/day, from about 100 mg/kg/day to about 125 mg/kg/day, from about 125 mg/kg/day to about 150 mg/kg/day, from about 150 mg/kg/day to about 175 mg/kg/day, or from about 175 mg/kg/day to about 200 mg/kg/day; and the dosage of γ-tocopherol ranges from about 100 mg/day to about 1000 mg/day, e.g., from about 100 mg/day to about 200 mg/day, from about 200 mg/day to about 300 mg/day, from about 300 mg/day to about 400 mg/day, from about 400 mg/day to about 500 mg/day, from about 500 mg/day to about 600 mg/day, from about 600 mg/day to about 700 mg/day, from about 700 mg/day to about 800 mg/day, from about 800 mg/day to about 900 mg/day, or from about 900 mg/day to about 1000 mg/day.

The dosage of other forms of vitamin E (e.g., β-tocopherol, δ-tocopherol, α-tocotrienol, β-tocotrienol, δ-tocotrienol, and γ-tocotrienol), if present in a subject formulation, can range from about 5 mg/day to about 1000 mg/day, e.g., from about 5 mg/day to about 10 mg/day, from about 10 mg/day to about 25 mg/day, from about 25 mg/day to about 50 mg/day, from about 50 mg/day to about 75 mg/day, from about 75 mg/day to about 100 mg/day, from about 100 mg/day to about 125 mg/day, from about 125 mg/day to about 150 mg/day, from about 150 mg/day to about 175 mg/day, from about 175 mg/day to about 200 mg/day, from about 200 mg/day to about 250 mg/day, from about 250 mg/day to about 500 mg/day, from about 500 mg/day to about 750 mg/day, or from about 750 mg/day to about 1000 mg/day, where the dosages given are for the individual isoforms of vitamin E.

Where a subject formulation comprises one or more omega-6 fatty acids, the dosage of omega-6 fatty acid can range from about 50 mg/day to about 1000 mg/day, e.g., from about 50 mg/day to about 75 mg/day, from about 75 mg/day to about 100 mg/day, from about 100 mg/day to about 150 mg/day, from about 150 mg/day to about 200 mg/day, from about 200 mg/day to about 250 mg/day, from about 250 mg/day to about 300 mg/day, from about 300 mg/day to about 350 mg/day, from about 350 mg/day to about 400 mg/day, from about 400 mg/day to about 450 mg/day, from about 450 mg/day to about 500 mg/day, from about 500 mg/day to about 600 mg/day, from about 600 mg/day to about 700 mg/day, from about 700 mg/day to about 800 mg/day, from about 800 mg/day to about 900 mg/day, or from about 900 mg/day to about 1000 mg/day.

Where a subject formulation comprises one or more omega-9 fatty acids, the dosage of omega-9 fatty acid can range from about 50 mg/day to about 500 mg/day, e.g., from about 50 mg/day to about 75 mg/day, from about 75 mg/day to about 100 mg/day, from about 100 mg/day to about 150 mg/day, from about 150 mg/day to about 200 mg/day, from about 200 mg/day to about 250 mg/day, from about 250 mg/day to about 300 mg/day, from about 300 mg/day to about 350 mg/day, from about 350 mg/day to about 400 mg/day, from about 400 mg/day to about 450 mg/day, or from about 450 mg/day to about 500 mg/day.

Where a subject formulation comprises α-lipoic acid, the dosage of α-lipoic acid can range from about 10 mg/kg/day to about 50 mg/kg/day, e.g., from about 10 mg/kg/day to about 20 mg/kg/day, from about 20 mg/kg/day to about 25 mg/kg/day, from about 25 mg/kg/day to about 30 mg/kg/day, from about 30 mg/kg/day to about 40 mg/kg/day, or from about 40 mg/kg/day to about 50 mg/kg/day; or can range from about 50 mg/day to about 1000 mg/day, e.g., from about 50 mg/day to about 75 mg/day, from about 75 mg/day to about 100 mg/day, from about 100 mg/day to about 150 mg/day, from about 150 mg/day to about 200 mg/day, from about 200 mg/day to about 250 mg/day, from about 250 mg/day to about 300 mg/day, from about 300 mg/day to about 350 mg/day, from about 350 mg/day to about 400 mg/day, from about 400 mg/day to about 450 mg/day, from about 450 mg/day to about 500 mg/day, from about 500 mg/day to about 600 mg/day, from about 600 mg/day to about 700 mg/day, from about 700 mg/day to about 800 mg/day, from about 800 mg/day to about 900 mg/day, or from about 900 mg/day to about 1000 mg/day.

Where a subject formulation comprises carnitine, the dosage of carnitine can range from about 20 mg/kg/day to about 75 mg/kg/day, e.g., from about 20 mg/kg/day to about 25 mg/kg/day, from about 25 mg/kg/day to about 30 mg/kg/day, from about 30 mg/kg/day to about 30 mg/kg/day, from about 40 mg/kg/day to about 50 mg/kg/day, from about 50 mg/kg/day to about 60 mg/kg/day, or from about 60 mg/kg/day to about 75 mg/kg/day; or can range from about 150 mg/day to about 3000 mg/day, e.g., from about 150 mg/day to about 200 mg/day, from about 200 mg/day to about 250 mg/day, from about 250 mg/day to about 300 mg/day, from about 300 mg/day to about 350 mg/day, from about 350 mg/day to about 400 mg/day, from about 400 mg/day to about 450 mg/day, from about 450 mg/day to about 500 mg/day, from about 500 mg/day to about 600 mg/day, from about 600 mg/day to about 700 mg/day, from about 700 mg/day to about 800 mg/day, from about 800 mg/day to about 900 mg/day, from about 900 mg/day to about 1000 mg/day, from about 1000 mg/day to about 1250 mg/day, from about 1250 mg/day to about 1500 mg/day, from about 1500 mg/day to about 1750 mg/day, from about 1750 mg/day to about 2000 mg/day, from about 2000 mg/day to about 2250 mg/day, from about 2250 mg/day to about 2500 mg/day, from about 2500 mg/day to about 2750 mg/day, or from about 2750 mg/day to about 3000 mg/day.

Subjects Suitable for Treatment

Subjects suitable for treatment with a subject method include individuals who have been diagnosed with a disorder such as apraxia, dyspraxia, autism spectrum disorder, attention deficit/hyperactivity disorder, dyslexia, or depression, sensory integration dysfunction; or an immune system disorder such as celiac disease, sprue, gluten sensitivity, a malabsorption syndrome, asthma, food allergy, leaky gut syndrome, or eczema; a cardiovascular disease; diabetes; or an inflammatory condition such as rheumatoid arthritis. Subjects suitable for treatment with a subject method also include individuals who have been previously treated (with a treatment method other than a subject method) for a disorder such as those listed above, but who have failed treatment (e.g., failed to respond to the treatment), who have relapsed, or in whom the previous treatment method was contraindicated (e.g., due to adverse reaction, etc.).

In some embodiments, the individual is a sub-adult human, e.g., an infant (e.g., from about 1 month of age to about 12 months of age); a toddler (e.g., from about 12 months of age to about 3 years of age); a pre-school age child (e.g., from about 3 years of age to about 5 years of age); a child from about 5 years of age to about 9 years of age; a pre-teen from about 9 years of age to about 12 years of age; or a teenager (e.g., from about 13 years of age to about 19 years of age). In other embodiments, the individual is an adult human, e.g., a human at least 18-20 years old.

In some embodiments, the individual is a sub-adult human who has been diagnosed with apraxia. In some embodiments, the individual is a sub-adult human who has been diagnosed with autism spectrum disorder.

In some embodiments, the individual exhibits gluten sensitivity. In some embodiments, the individual has a human leukocyte antigen (HLA) allele that is associated with gluten sensitivity. For example, in some embodiments, the individual has an HLA DQ1 allele. In some embodiments, the individual has elevated levels of anti-gliadin antibodies.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Case Study Patient A

A boy with the diagnoses of asthma, gastro-esophageal reflux, multiple food allergies, gluten-sensitivity (on a gluten/casein free diet since infancy), and global apraxia/dyspraxia (severe expressive speech disorder, and developmental coordination disorder—"clumsy child syndrome"), hypotonia, right sided weakness, and sensory integration dysfunction (poor propioception, abnormal vestibular sensation, and lack of appropriate pain sensation), chronic stearrhea, referred for early intervention evaluation and treatment at 17 months, responded slowly to conventional individual speech therapy, but learned quickly to communicate through sign language. At 23 months, he was non-verbal, at an expressive language level <9 months, frequently choked on his food after mouth stuffing, fell down 10-20 times and hour, often walking into walls and tables, had very low tone in his upper extremities, decreased deep tendon reflexes, tactile defensiveness and no pain sensation in his extremities. He was placed on omega 3/6/9 fatty acid therapy at 24 months of age. This child remained nonverbal despite several months of individual speech therapy, however he demonstrated excellent progress/improvement within days of initiation of PUFA supplementation in babbling, puckering, blowing bubbles, new word formation, and improved coordination/less falling down. After 1 month of PUFA supplementation, he experienced immediate regression within 48-72 hours (loss of speech ability and coordination) when fish oil supplements were stopped. He quickly regained these abilities when the PUFA supplements were reinstated and surpassed them on higher doses. He has subsequently demonstrated resolution of all neurodevelopmental symptoms after the addition of vitamin E (alpha and gamma).

Vitamin E (Vit E) supplementation was initiated after a literature search revealed that its deficiency causes a constellation of neurological symptoms that mirror those of apraxia of speech: articulation issues, poor coordination, low tone, and loss of proprioception, vestibular and pain sensation. However this connection has not been previously made. Within 6 weeks of vitamin E+PUFA supplements, this once severely apraxic/dyspraxic 36 month old child clinically presented as a normal 3 year old. Improvement in speech production/intelligibility and sentence length as well as improved coordination occurred rapidly. In addition a normalization of tone and sensory processing also occurred, including new processing of pain sensation in his extremities, which was previously absent. Residual symptoms of apraxia were apparent only on speech and OT assessments, and clinically with attempts at longer sentences and with tasks requiring complex motor planning.

The vit E dose was increased over several weeks and is now in the range recommended for neurological complications of vit E deficiency (100-200 mg/kg/day alpha-d-tocopherol). Sokol et al. Gastroenterology 1993; 104(6): 1727-35. Plasma levels of alpha-d-tocopherol before supplementation fell within the range of normal (12.9 ng/L), and did not change despite high dose supplementation. Currently at a total of 3000 IU alpha and 600 IU gamma tocopherol a day, divided into 3 doses, he is 90-100% intelligible and has experienced a complete resolution of speech, coordination and sensory abnormalities. All speech therapy and occupational therapy has been phased out due to this rapid and remarkable improvement within 5 months of beginning therapy, at which point it was felt by all evaluators to no longer be necessary.

Given that gut inflammation can cause malabsorption of key nutrients like vitamin E, a link to food allergy and gluten-sensitivity/celiac disease may exist. A metabolic work-up revealed a moderate/severe carnitine deficiency, a treatable condition that will impact fatty acid metabolism that is commonly described in children with autistic spectrum disorders. A secondary carnitine deficiency can occur in malabsorption syndromes like celiac disease. It is possible that gluten-sensitivity places children at increased risk for such neurological sequelae due to malabsorption. HLA testing revealed the gluten sensitive HLA gene (DQB1*0503), shown to be associated with gluten ataxia and other neurological complications of celiac disease. Carnitine supplementation was initiated approximately 6 weeks after vit E supplementation had begun and significant improvement in tone, strength and coordination has already occurred. It is difficult to assess the additional contribution of carnitine supplementation to overall improvement. However given further surges in speech and coordination with increased doses of vit E, the most significant contribution is felt to have come from vit E.

In addition to malabsorption, increased consumption of antioxidants due to oxidative stress (Traber (2006) Br J Nutr 96 Suppl 1:S34-7; Bruno (2006) Pathophysiology 13(3): 143-9; Brigelius-Flohe and Traber (1999) Faseb J 13(10): 1145-55; Traber (1997) Eur J Clin Invest 27(10):822-4; Traber (1999) Vitamin E. In: Shils M E, Olson J A, al. E, editors. Modern Nutrition in Health and Disease. 9th ed. Baltimore: Williams and Wilkens; p. 347-62) could also account for a potentially increased utilization of vit E and lack of change in plasma alpha tocopherol levels despite high-dose supplementation in this child. Abnormalities in alpha tocopherol transport into the brain and nervous system is another mechanism that could account for the neurological complications despite apparently adequate plasma levels. Genetic abnormalities of the alpha tocopherol transport protein have been described and are associated with neurological complications. Sokol R. Vitamin E deficiency and neurological disorders. In: Pacher L, Fuchs J, editors. Vitamin E in Health and Disease. New York: Marel Dekker; 1993. p. 815-49. Although a tocopherol transport protein has not yet been identified in the brain, it is assumed to exist. Regardless of the underlying mechanism, simple supplementation has led to a clinical cure in this child. However the underlying condition remains, as neurological symptoms rapidly reoccur even with a slight decrease in dosage of vit E supplementation.

The discovery of a moderate to severe carnitine deficiency may also be the result of a mild mitochondrial disorder. Subsequently additional antioxidants often part of a mitochondrial cocktail have been added to Patient A's daily regimen, including co-enzyme Q (100 mg/day), vitamin C (250 mg/day) and alpha-lipoic acid (300 mg/day) resulting in increased clarity of speech and improved energy level/stamina within 1 week of supplementation. Polyenylphosphatidylcholine (3 grams/day) is a molecule found in lecithin or egg believed to increase choline levels in the blood and brain and supports acetylcholine synthesis for proper neuronal and cell function and provides gastric mucosal protection. Decreased inflammation has been reported with its use, (Demirbilik et al, Intensive Care Med 2004, 30:1974-8), which may be of benefit in disorders involving increased oxidative stress. Patient A experienced a decreased in stearrhea within a week of supplementation, suggesting improvement in fat absorption. In addition Vitamin K (to prevent adverse effect of vitamin K antagonism by high dose vitamin E), a complete multi-vitamin combination (with selenium, zinc and high B-complex and additional fat soluble vitamins) was also added to the daily regimen. Although the most dramatic effects on symptoms of apraxia occurred with the use of omega 3+alpha and gamma tocopherol, the combination of carnitine, additional antioxidants and nutritional supplements let to global improvement in speech, coordination and sensory processing for Patient A that can not be explained by the intervention of speech and occupational therapy alone. Patient A has achieved a clinical cure of global apraxia with the above interventions. However during a recent illness of acute gastroenteritis that involved 2 days of vomiting which prohibited ingestion of the multiple nutritional supplements of this apraxia regimen, Patient A began to lose speech clarity/intelligibility and again began to demonstrate poor coordination with more frequent falls. The regression off supplements quickly resolved within 2-3 days, once the vomiting ceased and supplements were reintroduced. Dramatic neurological regressions have also been noted to occur with spoiled (oxidized/rancid) omega 3, benign viral illness stressors and conditions that trigger increased inflammation, including exposures to known food allergens in patient A (milk, gluten, yeast, mold, fungus). Specific food allergies have been confirmed through skin prick and patch testing, RAST testing and elimination diets, working closely with a pediatric allergist. Subsequent improvement in speech, coordination and behavior was noted with use of oral prednisone or dexamethasone for treatment of allergic reactions and asthma exacerbations triggered by food allergy. Further neurologic benefits were noted when the antifungal nystatin was used to treat oral candidiasis (from use of inhaled steroids as asthma therapy). Allergy to bakers/brewers yeast, mold and *aspergillus* was subsequently identified. Benefits from antifungals in this patient's case could be the result of decreased allergen load/exposure in a child with a yeast allergy.

Interventions: Speech Therapy and Occupational Therapy

At 21 months, 1:1 individual speech therapy (ST) was initiated at 60 minutes once a week and an additional 60 minutes once a week was spent working with an early intervention specialist who came to the home. ST was increased to 3 times a week between 27-36 months, and occupational therapy (OT) (1 hour) was started at twice a week for global dyspraxia, hypotonia and right-sided weakness. Steady improvement was made, especially after the addition of PUFA supplementation. However the child remained moderately apraxic/dyspraxic.

The Kaufman Speech Praxis Test (Table 1) was performed by a qualified speech and language pathologist at 24 month with scores in the ≤$3^{rd}$ percentile in all areas tested, demonstrating severe apraxia of speech. It was repeated 1 year later, approximately 4 weeks after vit E therapy was initiated. Overall intelligibility based on a 200 utterance collection to a familiar listener was calculated at 60% (previously<25%), <50% by a stranger in known contexts (previously>10%), <40% by stranger in unknown contexts (previously<10%). Mean length of utterance was calculated at 3.2 words. Although he still maintained a diagnosis of moderate apraxia that became more prominent with longer and more complex attempts at conversation, he made rapid, dramatic improved within 4 weeks of initiation of vit E supplementation. At the 36-month transition from regional center, this child still qualified for speech therapy (1 hour group) through the school district twice a week. Private 1:1 ST (1 hour) was planned to continue twice a week. Remarkable global improvement continued on vit E therapy as doses were increased. By later that same year, the apraxia diagnosis was no longer applicable. He was 90-100% intelligible even to strangers, and it was felt that ST and OT were no longer necessary, and school district-based services were cancelled. Repeat Kaufman testing reveals the highest attainable scores in all fields. Sentence structure on was calculated at the $99^{th}$ percentile, and speech therapy was discontinued.

TABLE 1

Improvements in Kaufman Praxis Test: Standard score (Percentile)

| | Kaufman Categories | | |
|---|---|---|---|
| | Pre Vitamin E (Age: 24 mos) | 4 wk Tx Vit E (Age: 35 mos) | 16 wk Tx Vit E (Age: 38 mos) |
| Oral Movement | 72 ($3^{rd}$) | 97 ($28^{th}$) | 110 ($40^{th}$)* |
| Simple Phonemic/Syllabic | 12 (<$3^{rd}$) | 106 ($42^{nd}$)* | Highest score already achieved |
| Complex Phonemic/Syllabic | 56 (<$3^{rd}$) | 83 ($16^{th}$) | 117 ($97^{th}$)* |
| Spontaneous Length & Complexity | 69 ($3^{rd}$) | 80 ($9^{th}$) | 111 ($58^{th}$)* |

Example 2

Impact of Vitamin E and Omega 3 Supplementation in Children with Verbal Apraxia

Verbal apraxia (VA) is a neurologically-based motor planning disorder of unknown etiology common in autism spectrum disorders (ASD) that anecdotally responds to omega 3 polyunsaturated fatty acid (PUFA) supplementation. Vitamin (vit) E deficiency causes symptoms that overlap those of VA. PUFAs in the cell membrane are vulnerable to lipid peroxidation and early destruction if vit E is not readily available, potentially leading to neurological sequelae. Inflammation of the gastrointestinal tract and gluten sensitivity may contribute to malabsorption of nutrients such as vit E and carnitine, contributing to fatty acid metabolism dysfunction and neurological abnormalities.

Objective: Determine efficacy of vit E and PUFA supplementation in children with VA.

Design/Methods: 50 children diagnosed with VA were treated with vit E+PUFA. 10 of these children were known to have ASD. A celiac panel, fat soluble vitamins, and carnitine level were obtained in patients having blood analyzed.

Results: Age ranged from 2-13 years, (majority<5 yrs), and 38/50 were boys. A history of gastrointestinal symptoms, sensory integration dysfunction, low muscle tone and coordination difficulties (dyspraxia) was commonly reported. Forty-eight families (96%) anecdotally reported dramatic improvements in a number of areas including speech, imitation, coordination, eye contact, behavior, sensory issues and the development of pain sensation. Two children experienced new tearful or aggressive behavior within 3 days of initiating vit E (400 IU/d) without apparent benefits in speech, and therapy was withdraw within a week. No other adverse effects were reported. Plasma alpha tocopherol levels varied in children tested (low in 2, high in 4, and normal in 4); however pre-treatment levels did not reflect clinical response. Low plasma carnitine was identified in 13/14 (93%) children. Antigliadin IgG antibodies were high in 9/11 (82%) children tested gluten-sensitivity HLA alleles were identified in 7 out of 7 boys screened. Two children reported vit D deficiency and early signs of rickets, and zinc deficiency was identified in 2 children. Abnormal fecal fat stool studies done in 4 children identified fat malabsorption in all 4 children.

Conclusions: Described here is a new disease paradigm of abnormal vit E and fatty acid metabolism causing neurological dysfunction in VA that responds to a safe nutritional intervention. The association of carnitine deficiency and gluten sensitivity with VA is a novel observation, suggesting that these children deserve a more comprehensive metabolic work-up than what is current standard practice.

Example 3

Characterization of a Neurodevelopmental Condition that Responds to Omega-3 and Vitamin E Supplementation The symptoms and metabolic anomalies of a cohort of children with VA that may respond to nutritional interventions were characterized. 183 children with VA (age range 2-15; median age 4 yrs, >20% ASD), were treated with vit E+PUFA. A celiac panel, fat soluble vitamins, and carnitine level was obtained in patients having blood analyzed. A common clinical phenotype of male predominance (80%), GI symptoms (diarrhea, constipation, abdominal pain, vomiting, gastroesophageal reflux), food allergy (skin-test/patch test/RAST test positive), sensory issues, low muscle tone and coordination difficulties emerged. 177 families (97%) anecdotally reported dramatic improvements in a number of areas including speech, imitation, coordination, eye contact, behavior, sensory issues and the development of pain sensation. Doses of vit E used range from 400 IU-3000 IU a day, with the majority of families using 800 IU a day divided into 2 doses, and an additional gamma tocopherol supplement (200-400 mg/day). No adverse events have occurred. A variety of blood testing was performed and reported in 23 children, with a summary of abnormal laboratory results described below.

1. Plasma Alpha-d-tocopherol levels: Broad range of levels reported in 12 children, both low (n=3), high (n=4) and normal (n=5) prior to supplementation. Pre-supplementation levels do not appear to reflect clinical response to vit E.

2. Plasma Carnitine levels: Low plasma carnitine (total & free) was reported in 19/24 (79%) children. Total carnitine levels were often 50-70% below the lower limit of normal, suggesting a moderate to severe deficiency. Although a carnitine deficiency is not uncommon in children with ASD, this is a novel observation in apraxia.

3. Antigliadin IgG antibodies: High in 15/19 (79%) children tested (8 had HLA testing done, and 100% revealed the presence of a DQ1 "gluten-sensitivity" gene, or celiac HLA DQ2).

4. Fat soluble vitamins: 3/4 reports of vitamin D deficiency, and early signs of rickets in 2 children. One child had signs of rickets identified on wrist films.

5. Plasma Selenium: One out of 2 boys tested had a significant selenium deficiency.

6. HLA testing: Performed on 8 boys, 100% of whom carried the "gluten-sensitivity" HLA (5 with DQ1 gene, known to be associated with neurological complications of gluten-sensitivity, and 3 with DQ2 associated with classic celiac disease). The frequency of this HLA genotype is high in our cohort, given its prevalence of about 30% in Caucasians. Antigliadin IgG antibodies were elevated in 7 of these boys on a gluten-containing diet. The seventh child, negative for antigliadin antibodies, had been gluten-free since infancy due to severe abdominal symptoms and a family history of gluten-intolerance. Intestinal biopsies done on 4 boys were negative for "classic" celiac disease, although one demonstrated villous atrophy.

7. Fat Malabsorption Syndrome: Identified on 7/9 boys on qualitative fecal fat studies.

8. Erythrocyte glutamine/glutamate ratio: Novel biomarker of oxidative stress (Morris et al Blood 2008), was very low in the one apraxic patient measured (prior to vit E therapy), suggesting significant oxidative stress with a ratio lower than the most ill patients with sickle cell disease (480 μM/241 μM); ratio=2 (normal=5.5±1.3).

9. Leukocyte redox studies: Low GSH and altered metabolism in immune cells in autism vs., normal controls has been documented (Jung et al, AJBB 2008), as noted by the Sulfur Amino Acid data below. In comparison, GSH is remarkably high in the apraxic and dyspraxic patients (n=2) after 1 year of PUFA/Vit E. Given the critical role of glutathione in maintaining redox balance and handling oxidative stress, a therapy that increases glutathione bioavailability is desirable.

|  | Control (n = 11) | Autism (n = 30) | Dypraxic Pt | Apraxic Pt |
| --- | --- | --- | --- | --- |
| Total Met (Met + Met – So) | 0.9 ± 0.3 | 1.3 ± 0.8 | 0.13841 | 0.12523 |
| SAM | 0.043 ± 0.02 | 0.028 ± 0.02 | 0.04670 | 0.03970 |
| SAH | 0.0096 ± 0.009 | 0.012 ± 0.008 | 0.01280 | 0.00700 |
| SAM/SAH ratio | 6.5 ± 4.6 | 3.3 ± 2.8 | 3.64844 | 5.67143 |
| Total Cys (Cys + (2*Cys2)) | 0.27 ± 0.12 | 0.16 ± 0.11 | 0.49 | 0.56 |
| Total GSH (GSH + (2*GSSG)) | 2.14 | 1.59 | 3.97 | 3.14 |
| Glutamine | 0.4 ± 0.17 | 0.34 ± 0.24 | 1.11 | 1.05 |
| Glutamate | 0.6 ± 0.26 | 0.75 ± 0.92 | 1.17 | 2.34 |
| Gln/Glu ratio | 0.67 ± 0.2 | 0.49 ± 0.56 | 0.94 | 0.45 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating apraxia and/or autism spectrum disorder, the method comprising orally administering to an individual in need thereof an effective amount of a formulation comprising:

a) eicosapentaenoic acid (EPA);

b) docosohexaenoic acid (DHA);

c) α-tocopherol;

d) γ-tocopherol;

wherein the ratio of EPA to DHA is in a range of from about 1.5:1 to about 5:1, wherein the α-tocopherol is present in an amount of from about 500 mg to about 3000 mg per unit dose, wherein the γ-tocopherol is present in an amount of from about 200 mg to about 1000 mg per unit dose, wherein the EPA is present in an amount of from about 500 mg to about 3000 mg per unit dose, wherein the DHA is present in an amount of from about 100 mg to about 400 mg per unit dose.

2. The method of claim 1, wherein the formulation is administered three times daily.

3. The method of claim 1, wherein the formulation is administered twice daily.

4. The method of claim 1, wherein the formulation is administered once daily.

5. The method of claim 1, wherein said administration is effective to increase the percentile score of at least one of oral movement score, simple phonemic/syllabic score, complex phonemic/syllabic score, and spontaneous length and complexity score.

6. The method of claim 1, wherein the formulation further comprises carnitine in an amount of from about 200 mg to about 3000 mg per unit dose.

7. The method of claim 1, wherein the formulation further comprises vitamin K in an amount of from about 100 μg to about 2 mg per unit dose.

8. The method of claim 1, wherein the formulation further comprises γ-linolenic acid in an amount of from about 50 mg to about 75 mg per unit dose.

9. The method of claim 1, wherein the formulation is in a dosage form selected from a tablet, a capsule, a powder, a gel, and a liquid.

10. The method of claim 1, wherein the individual is a human of from about 1 month to about 19 years of age.

11. The method of claim 1, wherein the individual is a human adult.

* * * * *